US009018371B2

(12) United States Patent
Jeong et al.

(10) Patent No.: US 9,018,371 B2
(45) Date of Patent: Apr. 28, 2015

(54) ADENOSINE DERIVATIVES, METHOD FOR THE SYNTHESIS THEREOF, AND THE PHARMACEUTICAL COMPOSITIONS FOR THE PREVENTION AND TREATMENT OF THE INFLAMMATORY DISEASES CONTAINING THE SAME AS AN ACTIVE INGREDIENT

(75) Inventors: Lak Shin Jeong, Seoul (KR); Hea Ok Kim, Seoul (KR); Kenneth A. Jacobson, Silver Spring, MD (US); Seung Ah Choe, Seoul (KR)

(73) Assignees: FM Therapeutics Co., Ltd., Seoul (KR); The United States of America, As Represented by the Secretary, Department of Health and Human Services, The Office of Technology Transfer, National Institutes of Health, Washington, DC (US)

( * ) Notice: Subject to any disclaimer, the term of this patent is extended or adjusted under 35 U.S.C. 154(b) by 790 days.

(21) Appl. No.: 12/530,086

(22) PCT Filed: Mar. 7, 2007

(86) PCT No.: PCT/KR2007/001131
§ 371 (c)(1),
(2), (4) Date: Feb. 10, 2010

(87) PCT Pub. No.: WO2008/108508
PCT Pub. Date: Sep. 12, 2008

(65) Prior Publication Data
US 2010/0137577 A1 Jun. 3, 2010

(51) Int. Cl.
C07H 19/16 (2006.01)
C07H 1/00 (2006.01)
C07D 473/34 (2006.01)

(52) U.S. Cl.
CPC .............. *C07D 473/34* (2013.01); *C07H 19/16* (2013.01)

(58) Field of Classification Search
CPC ....................................................... C07H 19/16
USPC ........................................... 536/27.62, 27.63
See application file for complete search history.

(56) References Cited

U.S. PATENT DOCUMENTS 5,688,774 A 11/1997 Jacobson et al.

FOREIGN PATENT DOCUMENTS

WO WO 2004/038006 A2 * 5/2004

OTHER PUBLICATIONS

WordNet Search 3.0, "prevent", also available at http://wordnet.princeton.edu/perl/webwn.*

Gunaga, P. et al., Organic Letters, "Stereoselective Functionalization of the 1'-Position of 4'-Thionucleosides", 2006, vol. 8, No. 19, pp. 4267-4270.*
Liu, H. et al., Canadian Journal of Chemistry, "Synthesis of zwitterionic selenium and sulfonium sulfates from D-mannose as potential glycosidase inhibitors", 2006, vol. 84, pp. 497-505.*
Smith, C. et al., Endocrine Reviews, "Coregulator Function: A Key to Understanding Tissue Specificity of Selective Receptor Modulators", 2004, vol. 25, No. 1, pp. 45-71.*
Jacobson, K. A. et al., J. Med. Chem., 35, 407-422, 1992.
Zhou Q. Y, et al., Proc. Natl. Acad. Sci., U.S.A., 89, 7432-7436, 1992.
Ramkumar, V. et al., J. Biol. Chem., 268, 168871-168890, 1993.
Abbracchio, M. P. et al., Mol. Pharmacol., 48, 1038-1045, 1995.
Baraldi, P. G. et al., Curr. Med. Chem., 12, 1319-1329, 2005.
Kim, S-K. et al., J. Mol. Graph. Model., 25, 562-577, 2006.
Jacobson, K. et al., "Structure-Activity Relationships of 9-Alkyladenine and Ribose-Modified Adenosine Derivatives at Rat A3 Adenosine Receptors", Journal of Medicinal Chemistry, American Chemical Society, US, vol. 38, No. 10, Jan. 1, 1995, pp. 1720-1735.
De Zwart, M. et al., "A Functional Screening of Adenosine Analogues at the Adenosine A2B Receptor: A Search for Potent Agonists", Nucleosides & Nucleotides, Marcel Dekker, Inc., U.S., vol. 17, No. 6, Jan. 1, 1998, pp. 969-985.
Chinese Patent Office Action dated Sep. 15, 2011, Application No. 200780052031.X, 10 pages.
Supplementary European Search Report, EP 07 71 5531, Jun. 9, 2011, 5 pages.
Jeong, et al., "Discovery of a New Nucleoside Template for Human A3 Adenosine Receptor Ligands: D-4'-thioadensosine Derivatives Without 4'-hydroxymethyl Group as Highly Potent and Selective Antagonists", J. Med. Chem. 2007, 50 (14), 3159-3162.
Jeong, et al., "Structure-Activity Relationships of Truncated D-and L-4'-thioadenosine Derivatives as Species-Independent A3 Adenosine Receptor Antagonists", J. Med. Chem. 2008, 51 (2), 6609-6613.
Zhao Wang et al, "Nucleoside-Derived Antagonists to $A_3$ Adenosine Mouse Receptors Intraocular Pressure and Act Across Species", Lower Experimental Eye Research 90, (2010) pp. 146-154, Science Direct, www.elsevier.com/locate/yexer.
Jiyoun Lee et al, "The Selective $A_3AR$ Antagonist LJ-1888 Ameliorates UUO-Induced Tubulointerstitial Fibrosis", The American Journal of Pathology, vol. 183, No. 5, Nov. 2013, ajp.amjpathol.org.

(Continued)

Primary Examiner — Shaojia Anna Jiang
Assistant Examiner — Bahar Craigo
(74) Attorney, Agent, or Firm — Blakely, Sokoloff, Taylor & Zafman LLP

(57) ABSTRACT

Disclosed are adenosine derivatives, methods for the synthesis thereof, and pharmaceutical compositions for the prevention and treatment of inflammatory diseases, comprising the same as an active ingredient. The adenosine derivatives have high binding affinity and selectivity for adenosine receptors, especially for $A_3$ adenosine receptors and act as $A_3$ adenosine receptor antagonists, and exhibit anti-inflammatory activity. Thus, the adenosine derivatives are useful in the prevention and treatment of inflammatory diseases.

14 Claims, 5 Drawing Sheets

(56) References Cited

OTHER PUBLICATIONS

Kenneth A. Jacobson et al, "Adenosine Receptors as Therapeutic Targets", Nature Reviews, vol. 5, pp. 247-264, Mar. 2006, Nature Publishing Group, www.nature.com/reviews/drugdisc.

Jeong et al, "Discovery of a New Nucleoside Template for Human $A_3$ Adenosine Receptor Ligands: D-4'-Thioadenosine Derivatives Without 4-Hydroxymethyl Group as Highly Potent and Selective Antagonists", Journal of Medical Chemistry, 2007, vol. 50, No. 14.

Australian Examiner's First Report dated May 8, 2012, Application No. 2007348394, 4 pages.

Australian Examiner's Second Report dated May 2, 2013, Application No. 2007348394, 3 pages.

Canadian Office Action dated Aug. 21, 2014, Application No. 2,680,179, 3 pages.

Journal of the Chemical Society, Perkin Transactions 1: Organic and Bio-Organic Chemistry, 1978, No. 5, pp. 500-505.

Chinese Second Office Action dated Apr. 16, 2012, Application No. 200780052031.X, 8 pages.

Chinese Fourth Office Action dated Mar. 19, 2013, Application No. 200780052031.X, 17 pages.

\* cited by examiner

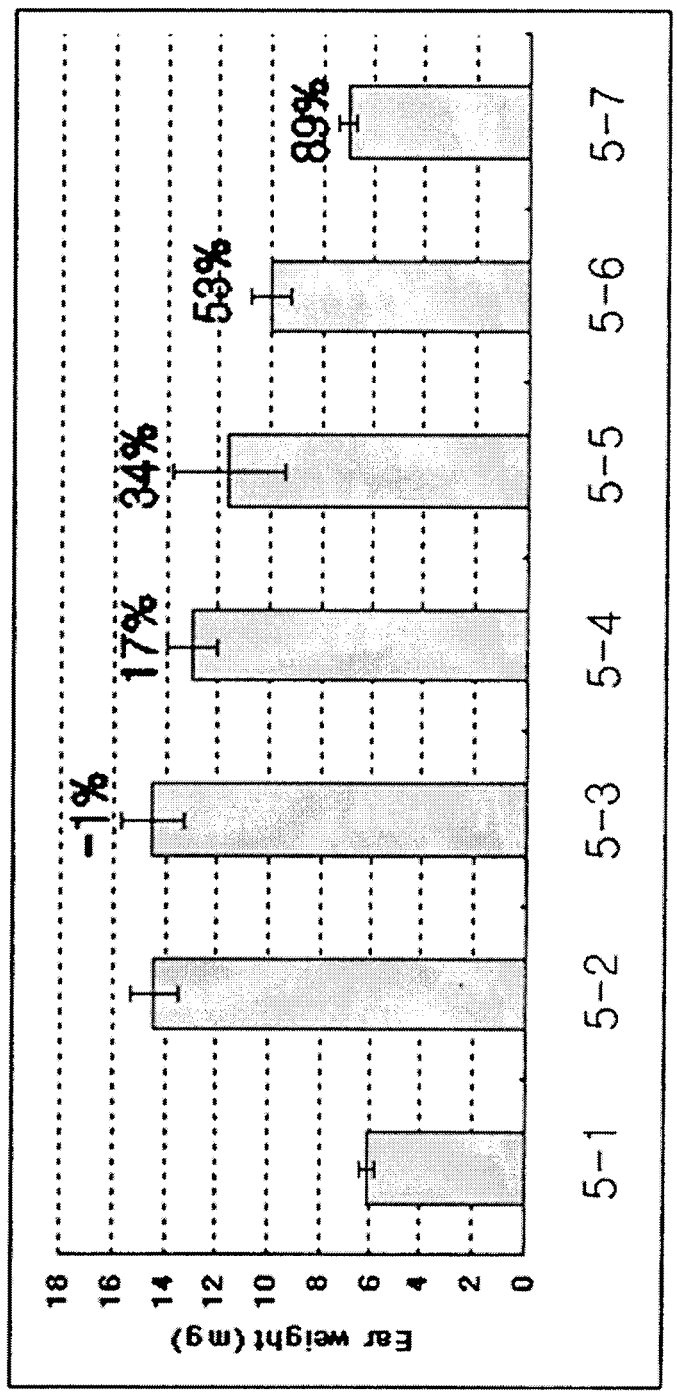

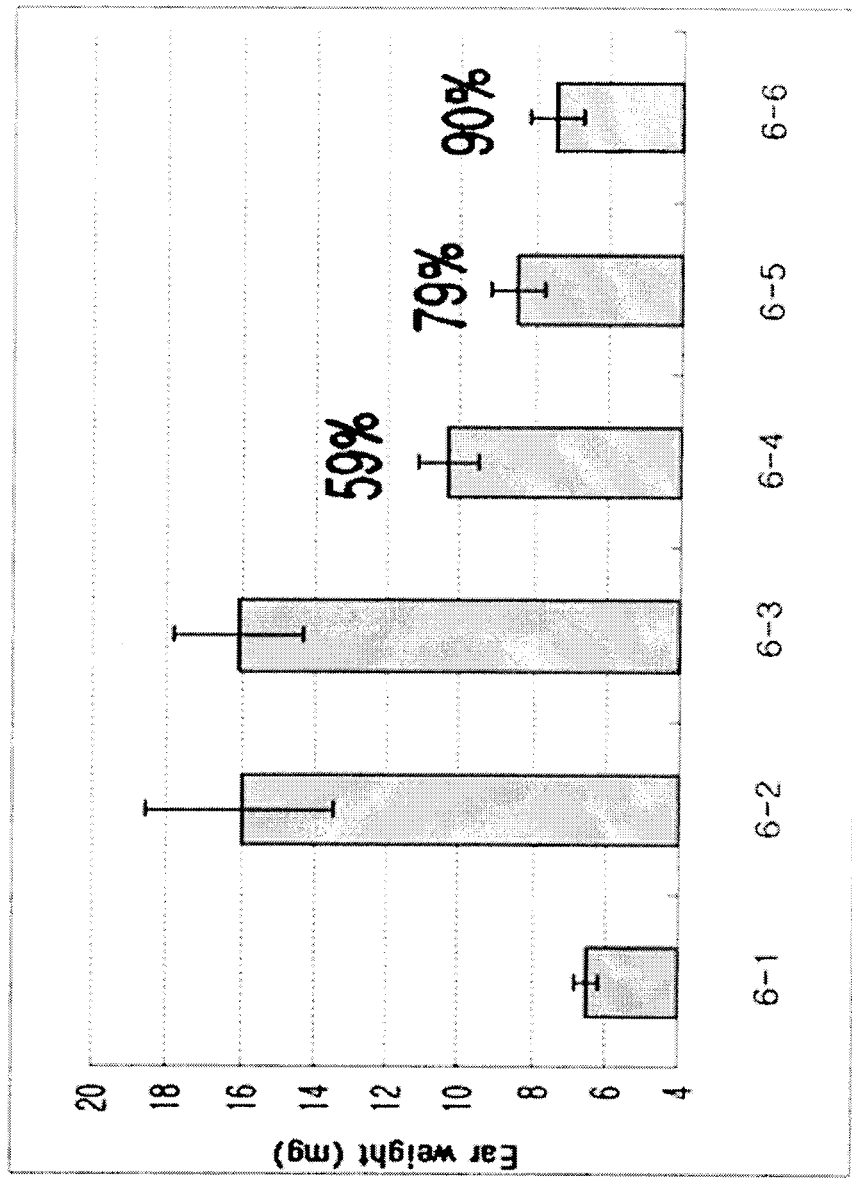

ADENOSINE DERIVATIVES, METHOD FOR THE SYNTHESIS THEREOF, AND THE PHARMACEUTICAL COMPOSITIONS FOR THE PREVENTION AND TREATMENT OF THE INFLAMMATORY DISEASES CONTAINING THE SAME AS AN ACTIVE INGREDIENT

CROSS REFERENCE TO RELATED APPLICATION

This patent application is a U.S. National Phase application under 35 U.S.C. §371 of International Application No. PCT/KR2007/001131, filed on Mar. 7, 2007, entitled ADENOSINE DERIVATIVES, METHOD FOR THE SYNTHESIS THEREOF, AND THE PHARMACEUTICAL COMPOSITIONS FOR THE PREVENTION AND TREATMENT OF THE INFLAMMATORY DISEASES CONTAINING THE SAME AS AN ACTIVE INGREDIENT.

TECHNICAL FIELD

The present invention relates to adenosine derivatives. More particularly, the present invention relates to adenosine derivatives and pharmaceutically acceptable salts thereof which show high binding affinity and selectivity for specific $A_3$ adenosine receptors. Also, the present invention relates to a method for synthesizing the adenosine derivatives and a pharmaceutical composition for the prevention and treatment of inflammatory diseases, comprising the adenosine derivatives or pharmaceutically acceptable salts thereof.

BACKGROUND ART

Adenosine is a ligand which regulates cell signaling, which accounts for various physiological functions through specific adenosine receptors located in the cell membrane. Adenosine, an extracellular substance, acts as a neurotransmitter in a variety of physical systems, typically functioning to compensate for overactivity of certain organs and protect the body from the harmful effects of stress (Jacobson, K. A. et al., J. Med. Chem., 35, 407-422, 1992). These functions are based on a part of the negative feedback loop in which adenosine, formed through the dephosphorylation of endocellular or extracellular ATP (adenosine triphosphate), decreases the cellular energy and increases oxygen supply. Adenosine plays an important role in maintaining the homeostasis of organs such as the brain, the heart and the kidneys. For example, when externally administered to the brain, an adenosine agonist was proven to show neuroprotective effects and was also found to be involved in pain, recognition, exercise and sleep.

Pharmacological research and molecular cloning studies have thus far revealed two classes (P1 and P2) of adenosine receptors. In mediating signal transduction, P1 receptors are adapted for adenosine while P2 receptors are adapted for ATP, ADP, UTP and UDP. Four subtypes of P1 receptors have been identified. They can be divided into $A_1$, $A_2$ and $A_3$ according to ligand affinity, distribution within the body, and functional pathway, and $A_2$ further into $A_{2A}$ and $A_{2B}$. These adenosine receptors are members of the G-protein-coupled receptor family. Pharmacological functions of adenosine $A_1$, $A_{2A}$ and $A_{2B}$ receptors have been revealed using various selective ligands. As for the $A_3$ receptor, it was first identified in 1992 (Zhou, Q. Y, et al., Proc. Natl. Acad. Sci., U.S.A., 89, 7432-7436, 1992) and its pathophysiological functions have been extensively studied.

Adenosine $A_1$ and $A_2$ receptor agonists, most derived from adenosine, have been intensively studied for use as hypotensive agents, therapeutics for mental illness and arrhythmia, lipid metabolism suppressant (therapeutics for diabetes) and neuroprotectives. On the other hand, their antagonists, derived from xanthine or in the form of two or more fused heterocyclic compounds, are developed as anti-asthmatics, anti-depressants, anti-arrhythmics, renal protectants, drugs for Parkinson's disease, and intelligence enhancers. Despite extensive study, only a few commercial products have been developed, including adenosine itself for the treatment of supraventricular tachycardia, and dipyridamole, the adenosine transfer inhibiting drug, which is used as a supplemental drug for warfarin in preventing blood coagulation after cardiotomy. The reason why little progress toward the commercialization of adenosine derivatives has been made is that because adenosine receptors are distributed throughout the body, and the activation thereof is accompanied by various pharmaceutical activities. In brief, there are no compounds that are able to activate only the adenosine receptors of a desired tissue.

The function of the adenosine $A_3$ receptor, the most recently identified, remains unknown, in contrast to the $A_1$ and $A_2$ receptors, the functions of which are well known. Extensive research has been conducted to develop selective ligands of the adenosine $A_3$ receptor. In this regard, three radiolabeled ligands [$^{125}$I]ABA ($N^6$-(4-amino-3-[$^{125}$I]iodobenzyl)-adenosine), [$^{125}$I]APNEA ($N^6$-2-(4-amino-3-[$^{125}$I] iodophenyl)-ethyl adenosine) and [$^{125}$I]AB-MECA ($N^6$-(4-amino-3-[$^{125}$I]iodobenzyl)-adenosine-5'-N-methylcarboxamide) are currently used for the pharmacological study of adenosine $A_3$ receptor. For example, it was found through research on the radiolabeled ligands that when expressed in Chinese Hamster Ovary (CHO) cells, the $A_3$ receptor inhibited adenylyl cyclase, an enzyme that produces cAMP from ATP. Also, when activated by agonists, the $A_3$ receptor was proven to mediate the activation of guanosine triphosphate-dependent phospholipase C, an enzyme which catalyzes the degradation of phosphatidyl inositol into inositol triphosphate and diacylglycerol (DAG) in the brain (Ramkumar, V. et al., J. Biol. Chem., 268, 168871-168890, 1993; Abbracchio, M. P. et al., Mol. Pharmacol., 48, 1038-1045, 1995). These findings indicate the possibility that there is a reaction pathway mediated by the $A_3$ receptor in cerebral ischemia when it is activated. The reason is that this second messenger system acts as a reaction pathway leading to nerve injury in cerebral ischemia. Also, $A_3$ receptor agonists are known to prevent cerebral diseases, such as epilepsy, and to protect the heart as well as inhibiting the release of TNF-α (tumor necrosis factor), an inflammation mediator, and the production of MIP-1α, interleukin-12 and interferon-γ, all acting as inflammation mediators. On the other hand, the inactivation of $A_3$ adenosine receptor causes the release of inflammation factors, such as histamine, from mast cells, bronchoconstriction, and the apoptosis of immune cells. Accordingly, $A_3$ adenosine antagonists have the possibility of being candidates as anti-inflammatory agents and anti-asthmatics. Therefore, compounds with pharmacological selectivity are believed to be drugs useful in the treatment of various diseases, including asthma, inflammation, cerebral ischemia, heart diseases, cancer, etc.

The nucleoside based compounds $N^6$-(3-iodobenzyl)-5'-(N-methylcarbamoyl)-adenosine (IB-MECA) and $N^6$-(3-iodobenzyl)-2-chloro-5'-(N-methylcarbamoyl)-adenosine (CI-IB-MECA) are representative human adenosine $A_3$ agonists, and exhibit higher affinity and selectivity for the $A_3$ adenosine receptor than for the $A_1$ and $A_2$ adenosine receptors. On the other hand, most potent and selective human $A_3$ adenosine receptor antagonists possess non-purinergic heterocyclic skeleton compounds. However, nearly all of the non-purinergic heterocyclic human $A_3$ adenosine antagonists are found to induce weak or ineffective activity through rat $A_3$ adenosine receptor and thus were unsuitable for evaluation in small animal models, which is indispensable to the development of drugs for clinical application (Baraldi, P. G. et al., Curr. Med. Chem., 12, 1319-1329, 2005).

le;2qHowever, since $A_3$ AR antagonists with nucleoside skeletons, in contrast to non-purinergic heterocyclic antagonists, exhibit high affinity and selectivity independent of species, the applicability thereof for animal test makes the nucleoside skeleton-based $A_3$ AR antagonists preferred drug candidates. Accordingly, there is a need for the development of selective $A_3$ antagonists based on nucleoside compounds.

Through various previous research, the present inventors discovered that nucleoside compounds must have an N-methylcarbamoyl group at position 5 of the sugar moiety and a base substituted with an arylamino group or alkylamino group at position 6 of the purine moiety for $A_3$ adenosine receptor agonism, as in the representative materials IB-MECA and Cl-IB-MECA. Since, since the N-methylcarbamoyl group at position 5 of the sugar moiety forms a hydrogen bond to cause a conformational change essential for the agonism of the receptors (Kim, S-K. et al., J. Mol. Graph. Model., 25, 562-577, 2006), compounds devoid of an N-methylcarbamoyl at position 5 of the sugar moiety are thought to be strong candidates for $A_3$ adenosine receptor antagonists.

Leading to the present invention, thorough and intensive research into $A_3$ adenosine receptor ligands and pharmaceutical effects, resulted in the finding that specific adenosine derivatives selected on the basis of the structure-activity relationship thereof have high binding affinity and selectivity for $A_3$ adenosine receptors compared to $A_1$ or $A_2$ adenosine receptors and can act as selective antagonists on $A_3$ adenosine receptors, thus showing high therapeutic effects on inflammatory diseases.

DISCLOSURE

Technical Problem

It is an object of the present invention to provide a novel adenosine derivative which acts as a selective $A_3$ adenosine receptor antagonist to show therapeutic activity on inflammatory diseases, a method for the synthesis thereof, and a pharmaceutical composition for the prevention and treatment of inflammatory diseases, comprising the same as an active ingredient.

Technical Solution

In accordance with an aspect of the present invention, there is provided a novel adenosine derivative, represented by the following Chemical formula 1, or a pharmaceutically acceptable salt thereof.

[Chemical Formula 1]

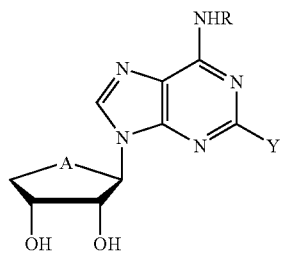

wherein, A is O or S; R is a linear or branched $C_1$~$C_5$ alkyl which is non-substituted or is independently or selectively substituted with one or more $C_6$~$C_{10}$ aryl groups, a benzyl which is non-substituted or is independently or selectively substituted with halogen or one or more linear or branched $C_1$~$C_4$ alkoxy groups, or a hydroxycarbonyl-substituted benzyl; and Y is H or a halogen atom.

In accordance with another aspect of the present invention, there is provided a method for the synthesis of the novel adenosine derivative or the pharmaceutically acceptable salt thereof.

In accordance with a further aspect of the present invention, there is provided an $A_3$ adenosine receptor antagonist comprising the adenosine derivative or pharmaceutically acceptable salt thereof.

In accordance with still a further aspect of the present invention, there is provided a pharmaceutical composition for the prevention and treatment of inflammatory diseases, comprising the adenosine derivative or the pharmaceutically acceptable salt thereof as an active ingredient.

Below, a detailed description is given of the present invention.

In accordance with an aspect thereof, the present invention pertains to an adenosine derivative compound represented by the following Chemical formula 1, a pharmaceutically acceptable salt thereof, and a composition comprising the compound or the salt as an active ingredient.

[Chemical formula 1]

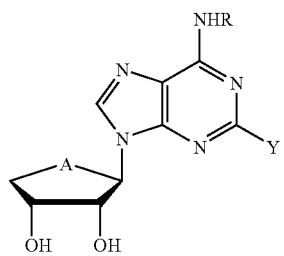

wherein,

A is O or S,

R is a linear or branched $C_1$~$C_5$ alkyl which is non-substituted or is independently or selectively substituted with one or more $C_6$~$C_{10}$ aryl groups, a benzyl which is non-substituted or is independently or selectively substituted with halogen or one or more linear or branched $C_1$~$C_4$ alkoxy groups, or a hydroxycarbonyl-substituted benzyl; and Y is H or a halogen atom.

In a preferable compound of Chemical formula 1,

A is O or S,

R is methyl, ethyl, propyl, naphthylmethyl, benzyl, benzyl independently or selectively substituted with a substituent selected from a group consisting of F, Cl, Br, I, $C_1$~$C_3$ alkoxy and combinations thereof, or toluic acid, and Y is H or Cl.

In a more preferable embodiment,

A is O or S,

R is methyl, ethyl, 1-naphthylmethyl, benzyl, 2-chlorobenzyl, 3-fluorobenzyl, 3-chlorobenzyl, 3-bromobenzyl, 3-iodobenzyl, 2-methoxy-5-chlorobenzyl, 2-methoxybenzyl, or 3-toluic acid, and Y is H or Cl.

Concrete examples of the novel adenosine derivatives according to a preferred embodiment of the present invention include:

1) (2R,3R,4S)-2-(2-chloro-6-(3-fluorobenzylamino)-9H-purin-9-yl)tetrahydrothiophen-3,4-diol;
2) (2R,3R,4S)-2-(2-chloro-6-(3-chlorobenzylamino)-9H-purin-9-yl)tetrahydrothiophen-3,4-diol;
3) (2R,3R,4S)-2-(6-(3-bromobenzylamino)-2-chloro-9H-purin-9-yl)tetrahydrothiophen-3,4-diol;
4) (2R,3R,4S)-2-(2-chloro-6-(3-iodobenzylamino)-9H-purin-9-yl)tetrahydrothiophen-3,4-diol;
5) (2R,3R,4S)-2-(2-chloro-6-(2-chlorobenzylamino)-9H-purin-9-yl)tetrahydrothiophen-3,4-diol;
6) (2R,3R,4S)-2-(2-chloro-6-(5-chloro-2-methoxybenzylamino)-9H-purin-9-yl)tetrahydrothiophen-3,4-diol;
7) (2R,3R,4S)-2-(2-chloro-6-(2-methoxybenzylamino)-9H-purin-9-yl)tetrahydrothiophen-3,4-diol;
8) (2R,3R,4S)-2-(2-chloro-6-(naphthalen-1-ylmethylamino)-9H-purin-9-yl)tetrahydrothiophen-3,4-diol;
9) 3-((2-chloro-9-((2R,3R,4S)-3,4-dihydroxytetrahydrothiophen-2-yl)-9H-purine-6-ylamino)methyl)benzoic acid;
10) 2-(2-chloro-6-methylamino-purin-9-yl)tetrahydrothiophen-3,4-diol;
11) (2R,3R,4S)-2-(6-(3-fluorobenzylamino)-9H-purin-9-yl)tetrahydrothiophen-3,4-diol;
12) (2R,3R,4S)-2-(6-(3-chlorobenzylamino)-9H-purin-9-yl)tetrahydrothiophen-3,4-diol;
13) (2R,3R,4S)-2-(6-(3-bromobenzylamino)-9H=purin-9-yl)tetrahydrothiophen-3,4-diol;
14) (2R,3R,4S)-2-(6-(3-iodobenzylamino)-9H-purin-9-yl)tetrahydrothiophen-3,4-diol;
15) (2R,3R,4R)-2-(6-(3-bromobenzylamino)-2-chloro-9H-purin-9-yl)tetrahydrofuran-3,4-diol; and
16) (2R,3R,4R)-2-(2-chloro-6-(3-iodobenzylamino)-9H-purin-9-yl)tetrahydrofuran-3,4-diol.

The novel adenosine derivative, represented by Chemical formula 1, in accordance with the present invention may be in the form of pharmaceutically acceptable salts. Useful are acid addition salts formed with a variety of pharmaceutically acceptable organic acids or inorganic acids. Examples of suitable organic acids include carboxylic acid, phosphoric acid, sulfonic acid, acetic acid, propionic acid, octanoic acid, decanic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzene sulfonic acid, 2-naphthalene sulfonic acid, methyl sulfonic acid, ethyl sulfonic acid, and dodecyl sulfonic acid. Suitable inorganic acids may be exemplified by hydrochloric acid, sulfuric acid, halogen acid, and phosphoric acid.

It should be noted that the adenosine derivatives represented by Chemical formula 1 are intended to include all salts, hydrates and solvates thereof as long as they can be prepared using conventional methods, as well as pharmaceutically acceptable salts thereof.

In accordance with another aspect thereof, the present invention pertains to a method for preparing the novel adenosine derivative represented by Chemical formula 1.

In an embodiment of this aspect, the adenosine derivative may be synthesized according to the following Scheme 1.

The method comprises reacting a compound of Chemical formula 2 with a silylated purine compound in the presence of a Lewis acid catalyst to produce a β-anomer compound of Chemical formula 3 (Step 1); adding hydrochloric acid to the β-anomer compound of Chemical formula 3 to produce a diol compound of Chemical formula 4 (Step 2); and reacting the diol compound of Chemical formula 4 with an amine compound in the presence of a base as a catalyst to produce the adenosine derivative (Step 3).

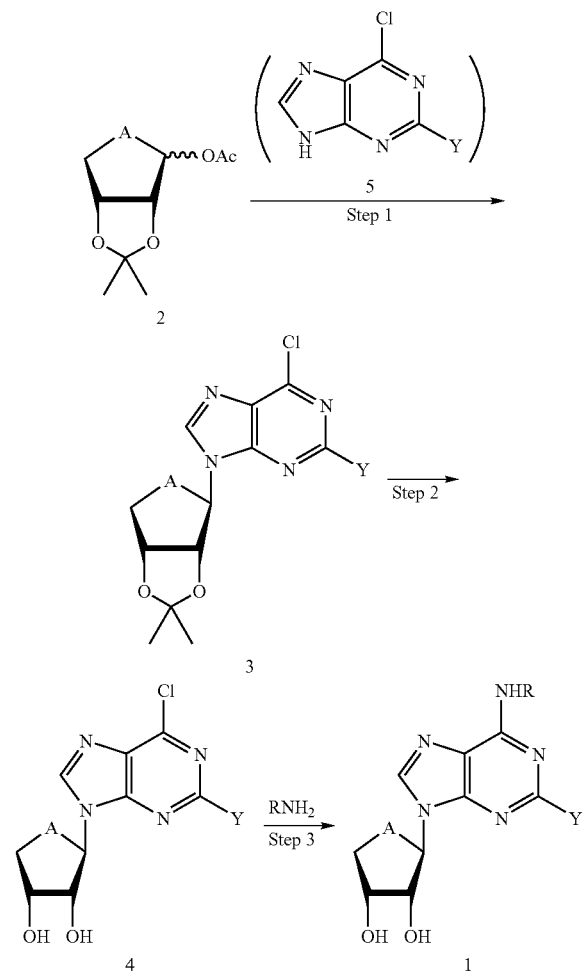

[Scheme 1]

wherein, A, R and Y are as defined above.

The method will be stepwise explained in detail.

In Step 1, the synthesis of the novel adenosine derivative starts with the compound of Chemical formula 2. In the presence of a Lewis acid as a catalyst, this starting material is reacted with a silylated purine compound to give the β-anomer compound of Chemical formula 3. Trimethylsilyl trifluoromethanesulfonate (TMSOTf) may be used as the Lewis acid catalyst. Dichloroethane, chloroform, acetonitrile, or dichloromethane is preferably used as the solvent in Step 1, with higher preference for dichloroethane. The silylated purine compound can be obtained by reaction between the purine compound of Chemical formula 5 and hexamethyldisilazane (HMDS) in the presence of ammonium sulfate as a catalyst.

In Step 2, acetonide is removed from the compound of Chemical formula 3 with HCl to give a diol compound of Chemical formula 4. Instead of HCl, acetic acid, sulfuric acid or p-toluene sulfonic acid may be used.

In Step 3, the diol compound of Chemical formula 4 obtained in Step 2 is reacted with an amine compound in the presence of a base as a catalyst to give the adenosine derivative.

Examples of the base catalyst useful in Step 3 include triethylamine, pyridine, N,N-dimethylaminopyridine, and 1,4-dioxane with preference for triethylamine. In addition, the reaction may be preferably conducted in a solvent selected from among lower alcohols such as methanol and ethanol, 1,4-dioxane, tetrahydrofuran and chloroform.

Depending on the kinds of the substituent A, the compound of Chemical formula 2 used as the starting material for the synthesis of the adenosine derivative according to the present invention may be synthesized through the reaction route of either Scheme 2 or 3.

When the substituent A is sulfur (S), Scheme 2 is taken for the synthesis of the starting material. As seen in Scheme 2, the synthesis of the starting material is accomplished by reacting the D-mannose compound of Chemical formula 6 with 2,2-dimethoxypropane in the presence of an acid as a catalyst to give the diacetonide compound of Chemical formula 7 (Step $a_1$); opening the compound of Chemical formula 7 obtained in Step $a_1$ in the presence of a reducing agent to afford the diol compound of Chemical formula 8 (Step $a_2$); mesylating the diol compound of Chemical formula 8 obtained in Step $a_2$ to afford the dimesyl compound of Chemical formula 9 (Step $a_3$); cyclizing the compound of Chemical formula 9 obtained in Step $a_3$ to afford the thiosugar compound of Chemical formula 10 (Step $a_4$); selectively hydrolyzing the compound of Chemical formula 10 obtained in Step $a_4$ to afford the diol compound of Chemical formula 11 (Step $a_5$); and converting the compound of Chemical formula 11 obtained in Step $a_5$ into an acetate compound of Chemical formula 2a in the presence of a catalyst (Step $a_6$).

[Scheme 2]

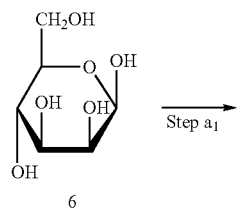

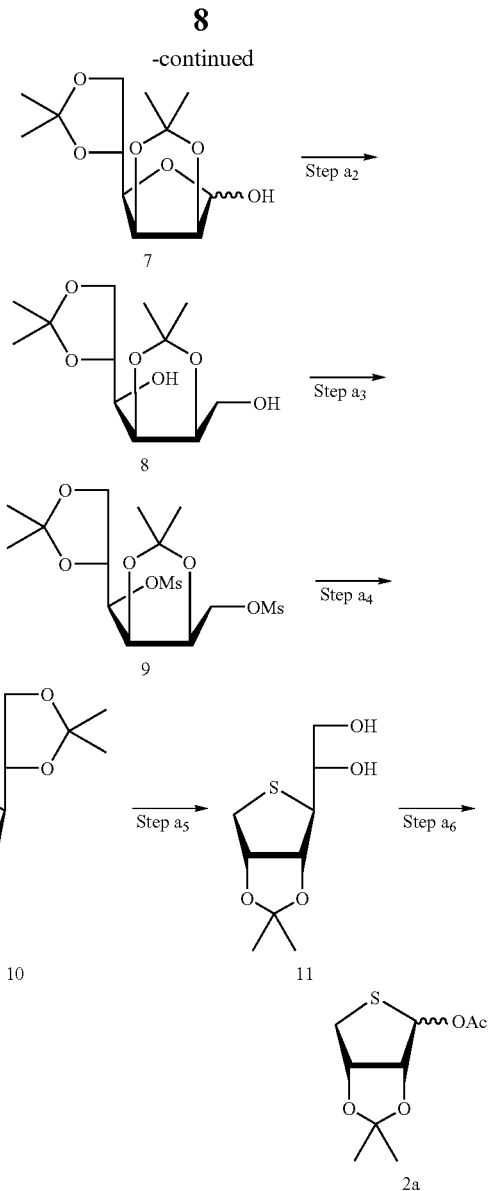

Compound 2a in Scheme 2 is identical to the compound of Chemical formula 2.

Below, the synthesis of Compound 2a will be further explained stepwise in greater detail.

As in Step $a_1$, the synthesis of Compound 2 starts from the D-mannose of Chemical formula 6. D-Mannose is reacted with 2,2-dimethoxypropane in the presence of an acid as a catalyst to give diacetonide compound of Chemical formula 7.

An acid in combination with anhydrous acetic acid, functioning to catalyze the conversion of D-mannose of Chemical formula 6 into the compound of Chemical formula 7, may be an inorganic acid, such as conc. sulfuric acid or hydrochloric acid, or an organic acid, such as p-toluenesulfonic acid.

In Step $a_2$, the compound of Chemical formula 7 is ring-opened in the presence of a reducing agent to afford the diol compound of Chemical formula 8.

The treatment of the compound of Chemical formula 7 with the reducing agent sodium borohydride produces the compound of Chemical formula 8. In lieu of sodium borohydride, a metal hydride, such as lithium aluminum hydride, or sodium sulfite may be used.

In Step $a_3$, the compound of Chemical formula 8 obtained in Step $a_2$ is mesylated into the dimesyl compound of Chemical formula 9.

The mesylation of the compound of Chemical formula 8 with methanesulfonylchloride (MsCl) into the compound of Chemical formula 9 is preferably conducted in an inert solvent, such as ethyl ether, petroleum ether, dichloromethane, tetrahydrofuran and N,N-dimethylformamideformamide.

In Step $a_4$, the compound of Chemical formula 9 obtained in Step $a_3$ is cyclized into a thiosugar compound of Chemical formula 10.

The compound of Chemical formula 10 can be obtained by reacting the compound of Chemical formula 9 with sodium sulfide. Alternatively, the compound of Chemical formula 10 can be achieved by substitution with a thio ester, such as methyl thioacetate, followed by reaction with sodium alkoxide. N,N-dimethylformamide or dimethylsulfoxide may be used as the solvent for Step $a_4$.

In Step $a_5$, the compound of Chemical formula 10 obtained in Step $a_4$ is selectively hydrolyzed into the diol compound of Chemical formula 11.

For the hydrolysis of the compound of Chemical formula 10 into the compound of Chemical formula 11, acetic acid may be used. In place of acetic acid, sulfuric acid, hydrochloric acid or p-toluene sulfonic acid may be used.

In Step $a_6$, the compound of Chemical formula 11 obtained in Step $a_5$ is converted into the acetate compound of Chemical formula 2a in the presence of a catalyst.

Conversion into the compound of the Chemical formula 2a is accomplished by reacting the compound of Chemical formula 11 with red tetraacetate ($Pd(OAc)_4$).

When the substituent A is oxygen (O), Scheme 3 is taken for the synthesis of the starting material 2. As seen in Scheme 3, the synthesis of the starting material is accomplished by reacting the compound of Chemical formula 12 with a reducing agent to afford the lactol compound of Chemical formula 13 (Step $b_1$); and reacting the compound of Chemical formula 13 obtained in Step $b_1$ with anhydrous acetic acid to afford an acetate compound of Chemical formula 2b (Step $b_2$).

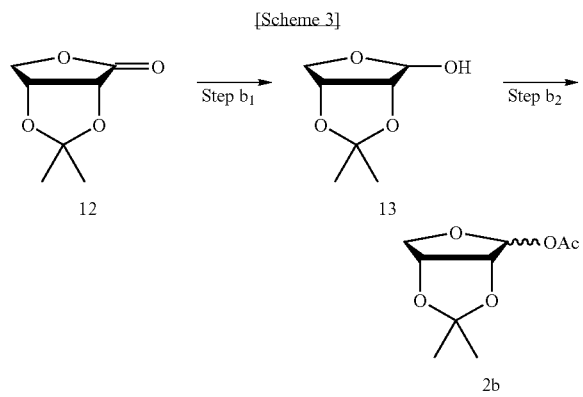

Compound 2b of Scheme 3 is identical to the compound of Chemical formula 2.

Below, the synthesis of Compound 2b will be further explained stepwise in greater detail.

In Step $b_1$, the compound of Chemical formula 12 is reduced into the lactol compound of Chemical formula 13.

For the reduction of the compound of Chemical formula 12, an easily synthesizable compound, into the compound of Chemical formula 13, diisobutylammonium hydride (DIBAL) may be used as a catalyst.

In Step $b_2$, the compound of Chemical formula 13 is reacted with anhydrous acetate to afford the acetate compound of Chemical formula 2b.

Thus, the compound of Chemical formula 2b can be obtained by reacting the lactol compound of Chemical formula 13 with acetate.

In accordance with a further aspect thereof, the present invention pertains to an $A_3$ adenosine receptor antagonist comprising the adenosine derivative represented by Chemical formula 1 or a pharmaceutically acceptable salt thereof as an active ingredient.

In accordance with still a further aspect thereof, the present invention pertains to a pharmaceutical composition for the prevention and treatment of inflammatory diseases, comprising the adenosine derivative represented by Chemical formula 1 or a pharmaceutically acceptable salt thereof as an active ingredient.

When expressed in Chinese Hamster Ovary (CHO) cells, $A_3$ adenosine receptors were found to inhibit adenylyl cyclase, an enzyme that produces cAMP from ATP. Also, when activated by agonists, the $A_3$ adenosine receptor was proven to mediate the activation of guanosine triphosphate-dependent phospholipase C, an enzyme which catalyzes the degradation of phosphatidyl inositol into inositol triphosphate and DAG in the brain (Ramkumar, V. et al., J. Biol. Chem., 268, 168871-168890, 1993; Abbracchio, M. P. et al., Mol. Pharmacol., 48, 1038-1045, 1995). These findings account for the possibility that there is a reaction pathway mediated by the $A_3$ adenosine receptor in cerebral ischemia when it is activated because this second messenger system serves as a reaction pathway for nerve injury in cerebral ischemia. Also, $A_3$ receptor agonists are known to prevent cerebral diseases, such as epilepsy, and to protect the heart as well as inhibiting the release of TNF-α (tumor necrosis factor), an inflammation mediator, and the production of MIP-1α, interleukin-12 and interferon-γ, all of which act as inflammation mediators. On the other hand, the inactivation of $A_3$ adenosine receptor causes the release of inflammation factors, such as histamine, from mast cells, bronchoconstriction, and the apoptosis of immune cells. Accordingly, $A_3$ adenosine antagonists have the possibility of being candidates as anti-inflammatory agents and anti-asthmatics.

The adenosine derivatives of the present invention were assayed for human adenosine receptor (hAR)-binding affinity and selectivity. In an assay for binding affinity (refer to Experimental Example 1), the adenosine derivatives of the present invention were found to have high binding affinity for human $A_3$ adenosine receptors (h$A_3$ AR), but low affinity for $A_1$ and $A_{2A}$ adenosine receptors, thereby showing high selectivity. Particularly, the compound of Example 12 shows the highest binding affinity for h$A_3$ AR with $K_i$ determined at 1.50±0.40 nM, followed by the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM) in decreasing order of binding affinity. Also, the compound of Example 4 was measured to have high binding affinity for the rat $A_3$ adenosine receptor expressed in CHO cells ($K_{21}$=3.89±1.15 nM). In addition, the compounds of Examples 15 and 16, both adenosine derivatives in the form of 4'-O oxonucleoside, show high binding affinity and selectivity (see Table 1).

In assays for anti-inflammatory activity (refer to Experimental Examples 3-6), the adenosine derivatives of the present invention were found to have anti-inflammatory activity, although this was low compared to that of the control hydrocortisone.

When administered to mice treated with TPA in the ears, the compounds of Examples 2 to 4, diluted in acetone, were observed to decrease inflammation of the ears to some degree (see FIG. 2). In addition, the compounds of Examples 1 and 6 were found to have anti-inflammatory activity four or more times that of the compounds of Examples 2 to 4, as measured on the basis of inhibition percentage (FIG. 3).

In an assay for anti-inflammatory activity, the compounds of Examples 5, 7 and 8, diluted at a concentration of 0.5% in a mixture of distilled water and acetone (1:4), were measured to have percentages of inflammation inhibition of 17%, 34% and 53%, respectively (FIG. 4). The compounds of Examples 15 and 16, diluted at a concentration of 0.5% in a mixture of DMSO and acetone (1:9), were measured to have percentages of inflammation inhibition of 59% and 79%, respectively (FIG. 5). Based on the observations in the assay, the adenosine derivatives of the present invention were proven to have anti-inflammatory activity.

Having high binding affinity and selectivity for $A_3$ adenosine receptors, thus, the adenosine derivatives, represented by Chemical formula 1, according to the present invention, can be effectively used as $A_3$ adenosine receptor antagonists. Further, the adenosine derivatives of the present invention exert antagonism on $A_3$ adenosine receptors, showing anti-inflammatory activity, and thus are useful in the prevention and treatment of inflammatory diseases.

The inflammatory disease to which the adenosine derivatives of the present invention can be effectively applied include acute and chronic inflammatory diseases, such as ulcerative inflammation, exudative inflammation, purulent inflammation, hemorrhagic inflammation, and hyperplastic inflammation.

With regard to pharmaceutical compositions comprising the adenosine derivative of the present invention or pharmaceutically acceptable salts thereof, they are formulated into dosage forms with expedients, as will be explained with the following examples, which are illustrative only, and are not intended to limit the present invention. The compositions of the present invention may be administered systemically or topically.

The compound of the present invention may be clinically administered in oral or non-oral forms. It is usually formulated in combination with a diluent or excipient, such as a filler, a thickening agent, a binder, a wetting agent, a disintegrant, a surfactant, etc. Solid agents intended for oral administration of the compound of the present invention may be in the form of tablets, pills, powders, granules, capsules, and the like. These solid agents are formulated in combination with at least one excipient such as starch, calcium carbonate, sucrose, lactose, or gelatine. Besides, a lubricant, such as magnesium stearate, talc and the like, may be added, as well. Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid agents for the oral administration of the compound of the present invention.

Also, non-oral dosage forms of the compound of the present invention include injections, emulsions, inhalations, and suppositories. For injections, sterile aqueous solutions, non-aqueous solvents, and suspensions made from propylene glycol, polyethylene glycol, vegetable oils such as olive oil, and esters such as ethylolate may be used. The basic materials of suppositories include witepsol, macrogol, tween 61, cacao paper, laurin paper, glycerol, and gelatine. The compound of the present invention may be formulated into ointments or cream for topical application.

Depending on the conditions of patients, including age, body weight, sex, administration route, and disease severity, the administration dose of the compound of the present invention to humans may vary. Typically, the compound of the present invention is administered at a dose from 0.001 to 100 mg per kg of body weight a day and preferably at a dose from 0.01 to 30 mg per kg of body weight a day. The compound may be administered in a single dose or in divided doses per day. The compound of the present invention is contained in an amount from 0.0001 to 10% by weight based on the total weight of the composition and preferably in an amount from 0.001 to 1% by weight. Also, the administration route is dependent on patient's health state and disease severity.

DESCRIPTION OF DRAWINGS

The application of the preferred embodiments of the present invention is best understood with reference to the accompanying drawings, in which like reference numerals are used for like and corresponding parts, wherein:

FIG. 4 is a graph showing the anti-inflammatory activity of the compounds of the present invention (Examples 5, 7 and 8) in animal tests; and FIG. 5 is a graph showing the anti-inflammatory activity of the compounds of the present invention (Examples 15 and 16) in animal tests.

MODE FOR INVENTION

Figure 1:
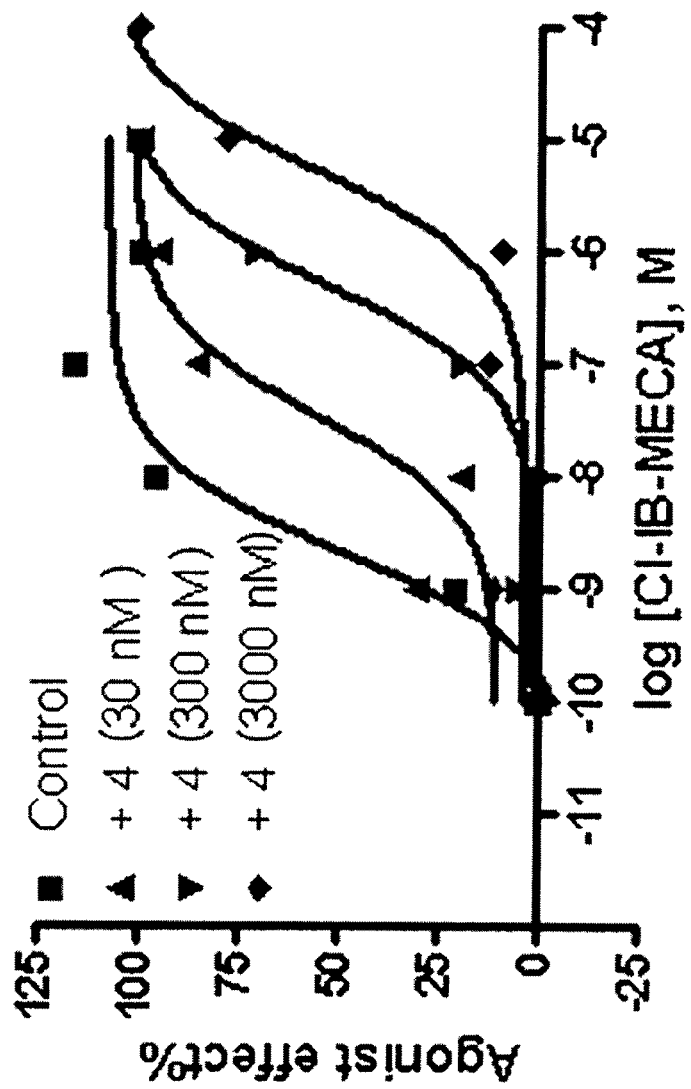
FIG. 1 is a graph showing the antagonist effect of the compound of Example 4 on the CHO cells treated with the agonist Cl-IB-MECA.

A better understanding of the present invention may be obtained in light of the following examples which are set forth to illustrate, but are not to be construed to limit the present invention.

Synthesis of the Starting Material

Preparation Example 1

Preparation of (3aR,4R,6aS)-2,2-Ddimethyltetrahydrothieno[3,4-d][1,3]dioxol-4-yl acetate Step $a_1$. Preparation of (3aR,4R,6R,6aR)-6-(2,2-dimethyl-1,3-dioxolan4-yl)-2,2-dimethyl-tetrahydrofuro[3,4-d][1,3]dioxol-4-ol To acetone (50 ml) were added D-mannose (1.74 g, 6.52 mmol) and 2,2-dimethoxypropane (2.45 ml, 19.55 mmol) with stirring, followed by cooling the solution to 0° C. To the solution was dropwise added conc. sulfuric acid (0.45 g, 1.96 mmol). The resulting reaction mixture was stirred at room temperature for 24 hrs, followed by neutralization with triethyl amine and concentration in a vacuum. The concentrate was purified by silica gel column chromatography using a mixture of hexane:ethylacetate (1:1, v/v) as an elution solvent to afford the object compound as a white solid (1.61 g, 95%). m.p. 120.3-120.5° C.

$^1$H-NMR (CDCl$_3$) δ 5.34 (s, 1H), 4.76-4.79 (m, 1H), 4.58 (d, 1H, J=6.0 Hz), 4.34-4.39 (m, 1H), 4.15 (dd, 1H, J=3.6, 7.2 Hz), 4.00-4.08 (m, 2H);

$[α]^{25}_D$ 11.71 (c 0.11, CH$_2$Cl$_2$);

FAB-MS m/z 261 [M+H]$^+$.

Step a$_2$. Preparation of (1R)-(2,2-dimethyl-1,3-dioxolan4-yl)((4R,5S)-5-(hydroxymethyl)-2,2-dimethyl-1,3-dioxolan-4-yl)methanol (3aR,4R,6R,6aR)-6-(2,2-dimethyl-1,3-dioxolan4-yl)-2,2-dimethyl-tetrahydrofuro[3,4-d][1,3]dioxol-4-ol (1.50 g, 5.76 mmol), prepared in Step a$_1$, was carefully added to ethanol (25 ml) and the solution was cooled to 0° C. To the solution was added sodium borohydride (NaHB$_4$, 440 mg, 11.53 mmol), followed by stirring the solution at room temperature for 2 hrs. The reaction mixture was neutralized with acetic acid and concentrated in a vacuum. The concentrate was extracted with ethylacetate and water. The organic layer was dried over anhydrous magnesium sulfate (MgSO$_4$), filtered and concentrated in a vacuum. The concentrate was purified by silica gel column chromatography using a mixture of hexane:ethylacetate (1:1, v/v) as an elution solvent to afford the object compound in a syrup form (1.38 g, 92%).

$^1$H-NMR (CDCl$_3$) δ 4.33 (dd, 1H, J=1.6, 7.2 Hz), 4.24-4.28 (m, 1H), 4.06-4.13 (m, 2H), 3.92-3.97 (m, 1H), 3.76-3.85 (m, 2H), 3.59-3.61 (m, 1H), 1.48 (s, 3H), 1.38 (s, 3H), 1.36 (s, 3H), 1.33 (s, 3H);

$[α]^{25}_D$-3.88 (c 0.44, CH$_2$Cl$_2$);

FAB-MS m/z 263 [M+H]$^+$.

Step a$_3$. Preparation of (1R)-(2,2-dimethyl-1,3-dioxolan4-yl)((4S,5S)-2,2-dimethyl-5-((methylsulfonyloxy)methyl)-1,3-dioxolan4-yl)methylmethanesulfonate (1R)-(2,2-dimethyl-1,3-dioxolan4-yl)((4R,5S)-5-hydroxymethyl)-2,2-dimethyl-1,3-dioxolan4-yl)methanol (38.52 g, 146.85 mmol), prepared in Step a$_2$, and 4-dimethylaminopyridine (4-DMAP, 5.38 mg, 44.06 mmol) were added to a mixture of dichloromethane (300 ml) and triethylamine (163.75 ml, 1.17 mol), and the solution was stirred and cooled to 0° C. To this was dropwise added dimethanesulfonyl chloride (47.59 ml, 587.42 mmol). After stirring at room temperature for 1 hr, the reaction mixture was extracted with dichloromethane and washed with a saturated sodium hydrogen carbonate (NaHCO$_3$) solution. The organic layer thus obtained was dried over anhydrous magnesium sulfate (MgSO$_4$), filtered and concentrated in a vacuum. The dimesyl compound thus produced, having the form of a brown syrup, was purified through silica gel column chromatography using a mixture of hexane:ethylacetate (5:1, v/v) as an elution solvent to afford the object compound in syrup form (57.83 g, 94%).

$^1$H-NMR (CDCl$_3$) δ 4.75 (pseudo t, 1H, J=7.4 Hz), 4.33-4.45 (m, 4H), 4.06-4.20 (m, 3H), 3.12 (s, 3H), 3.07 (s, 3H), 1.51 (s, 3H), 1.43 (s, 3H), 1.37 (s, 3H), 1.33 (s, 3H);

$[α]^{25}_D$ 38.32 (c 0.29, CH$_2$Cl$_2$);

FAB-MS m/z 419 [M+H]$^+$.

Step a$_4$. Preparation of (3aR,4S,6aS)-4-(2,2-dimethyl-1,3-dioxolan4-yl)-2,2-dimethyltetrahydrothieno[3,4-d][1,3]dioxol (1R)-(2,2-dimethyl-1,3-dioxolan4-yl)((4S,5S)-2,2-dimethyl-5-((methylsulfonyloxy)methyl)-1,3-dioxolan4-yl)methyl methanesulfonate (993.80 g, 2.23 mmol), prepared in Step a$_3$, was dissolved in DMF (50 ml). Following the addition of sodium sulfide (348.30 g, 4.46 mmol) thereto, the solution was stirred at 80° C. under a reflux condition overnight. Thereafter, the solvent was removed in a vacuum and the residue was extracted with ethyl acetate and water. The organic layer was dried over anhydrous magnesium sulfate (MgSO$_4$), filtered, and concentrated in a vacuum. The concentrate was purified through silica gel column chromatography using a mixture of hexane:ethylacetate (8:1, v/v) as an elution solvent to afford the object compound in a syrup form (453.0 mg, 78%).

$^1$H-NMR (CDCl$_3$) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);

$[α]^{25}_D$-96.04 (c 0.20, CH$_2$Cl$_2$);

FAB-MS m/z 261 [M+H]$^+$.

Step a$_5$. Preparation of 1-((3aR,4S,6aS)-2,2-dimethyltetrahydrothieno[3,4-d][1,3]dioxol-4-yl)ethan-1,2-diol (3aR,4S,6aS)-4-(2,2-dimethyl-1,3-dioxolan-4-yl)-2,2-dimethyltetrahydrothieno[3,4-d][1,3]dioxol (21.78 g, 83.66 mmol), prepared in Step a$_4$, was dissolved in a 60% aqueous acetic acid solution (250 ml), followed by stirring the solution at room temperature for 2 hrs. The reaction mixture was concentrated in a vacuum and the concentrate was purified through silica gel column chromatography using a mixture of hexane:ethylacetate (1:2, v/v) as an elution solvent to afford the object compound as a white solid (14.85 g, 81%).

$^1$H-NMR (CDCl$_3$) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);

$[α]^{25}_D$-96.04 (c 0.20, CH$_2$Cl$_2$);

FAB-MS m/z 261 [M+H]$^+$.

Step a$_6$. Preparation of (3aR,4R,6aS)-2,2-dimethyltetrahydrothieno[3,4-d][1,3]dioxol-4-yl acetate 1-((3aR,4S,6aS)-2,2-dimethyltetrahydrothieno[3,4-d][1,3]dioxol-4-yl)ethan-1,2-diol (14.85 g, 67.41 mmol), prepared in Step a$_5$, was dissolved in ethylacetate (300 ml) and cooled to 0° C. To the solution was added red tetraacetate (Pb(OAc)$_4$, 157.31 g, 337.06 mmol), followed by stirring at room temperature overnight. The reaction mixture was filtered through a Celite filter and the filtrate was diluted in ethyl acetate. The organic layer was diluted in dichloromethane, washed with a saturated aqueous sodium hydrogen carbonate (NaHCO$_3$) solution, dried over anhydrous magnesium sulfate, and concentrated in a vacuum. The concentrate was purified through silica gel column chromatography using a mixture of hexane:ethylacetate (8:1, v/v) as an elution solvent to afford the object compound in a syrup form (8.82 g, 60%).

$^1$H-NMR (CDCl$_3$) δ 5.03 (dd, 1H, J=5.6, 9.6 Hz), 4.79 (dd, 1H, J=5.6, 8.8 Hz), 3.21-3.27 (m, 2H), 3.01 (dt, 2H, J=0.8, 12.8 Hz), 2.05 (s, 3H), 1.50 (s, 3H), 1.31 (s, 3H);

$[α]^{25}_D$-258.15 (c 0.18, CH$_2$Cl$_2$);

FAB-MS m/z 218 [M]$^+$.

Preparation Example 2

Preparation of (3aS,4S,6aS)-2,2-Dimethyl-tetrahydrofuro[3,4-d][1,3]dioxol-4-yl acetate

Step b₁. Preparation (3aR,4R,6aR)-2,2-dimethyl-tetrahydrofuro[3,4-d][1,3]dioxol-4-ol 2,3-O-isopropylidene-D-erythronolactone (1.04 g, 6.42 mmol) was dissolved in toluene (20 ml), followed by the addition of 1 M diisobutylammonium hydride (DIBAL)/THF to the solution at −78° C. The reaction mixture was stirred at the same temperature for 30 min and methanol was slowly added until the reaction terminated. The suspension was filtered through a Celite filter and the filtrate was extracted with ethyl acetate and water, followed by silica gel column chromatography using a mixture of hexane:ethylacetate (3:1, v/v) to give the object compound in syrup form (1.94 g, 96%).

$^1$H-NMR (CDCl$_3$) δ 5.39 (s, 1H), 4.82 (dd, 1H, J=3.6, 6.0 Hz), 4.55 (d, 1H, J=6.0 Hz), 4.05 (dd, 1H, J=3.6, 10.2 Hz), 4.00 (d, 1H, J=10.0 Hz), 1.45 (s, 3H), 1.30 (s, 3H).

Step b₂. Preparation of (3aS,4S,6aS)-2,2-dimethyl-tetrahydrofuro[3,4-d][1,3]dioxol-4-yl acetate To a solution of the lactol compound (875.9 mg, 5.47 mmol), prepared in Step in pyridine (10 ml) was added anhydrous acetic acid (0.67 ml, 6.56 mmol) at 0° C. The reaction mixture was stirred at room temperature for 3 hrs and concentrated in a vacuum. The concentrate was extracted with ethylacetate and water and the organic layer was dried over anhydrous magnesium sulfate and concentrated in a vacuum. The residue was purified by silica gel column chromatography using a mixture of hexane:ethylacetate (8:1, v/v) to give the object compound in a syrup form (702.1 mg, 65%).

$^1$H-NMR (CDCl$_3$) δ 6.16 (s, 1H), 4.86 (dd, 1H, J=3.6, 6.0 Hz), 4.66 (d, 1H, J=6.0 Hz), 4.12 (d, 1H, J=6.4 Hz), 3.99 (dd, 1H, J=3.6, 10.8 Hz), 2.05 (s, 3H), 1.48 (s, 3H), 1.33 (s, 3H).

Example 1

Synthesis of (2R,3R,4S)-2-(2-Chloro-6-(3-fluorobenzylamino)-9H-purin-9-yl)tetrahydrothiophen-3,4-diol

Step 1. Preparation of 2,6-dichloro-9-((3aR,4R,6aS)-2,2-dimethyltetrahydrothieno[3,4-d][1,3]dioxol-4-yl)-9H-purine A solution of 2,6-dichloropurine (2.29 g, 22.12 mmol) and ammonium sulfate (438 mg, 3.32 mmol) in hexamethyldisilazane (HMDS, 50 ml) was fluxed overnight under inert, dry conditions. The resulting reaction mixture was concentrated in a vacuum and the solid mixture thus formed was re-dissolved in cold 1,2-dichloroethene (20 ml). To this solution were dropwise added a solution of (3aR,4R,6aS)-2,2-dimethyltetrahydrothieno[3,4-d][1,3]dioxol-4-yl acetate (1.41 g, 11.06 mmol), obtained in Preparation Example 1, in 1,2-dichloroethane (20 ml), and then trimethylsilyl trifluoromethanesulfonate (TMSOTf, 4.0 ml, 22.12 mmol). The resulting solution was stirred at 0° C. for 30 min and then at room temperature for 1 hr, and heated at 80° C. for 2 hrs with stirring. The reaction mixture was cooled, diluted in dichloromethane and washed with a saturated aqueous sodium hydrogen carbonate (NaHCO$_3$) solution. The organic solvent was dried over anhydrous magnesium sulfate (MgSO$_4$) and concentrated in a vacuum to give a residue in the form of a yellow syrup. The residue was purified through silica gel column chromatography using a mixture of dichloromethane:methanol (50:1, v/v) as an elution solvent to afford the object compound in the form of a foam (3.03 g, 79%).

UV (CH$_2$Cl$_2$) λ$_{max}$ 275.0 nm;

$^1$H-NMR (CDCl$_3$) δ 8.17 (s, 1H), 5.87 (s, 1H), 5.32 (pseudo t, 1H, J=4.8 Hz), 5.21 (d, 1H, J=5.6 Hz), 3.79 (dd, 1H, J=4.4, 12.8 Hz), 3.26 (d, 1H, J=13.2 Hz), 1.59 (s, 3H), 1.36 (s, 3H);

[α]$^{25}_D$-42.04 (c 0.16, CH$_2$Cl$_2$);

FAB-MS m/z 347 [M+H]$^+$.

Step 2. Preparation of (2R,3S,4S)-2-(2,6-dichloro-9H-purin-9-yl)tetrahydrothiophen-3,4-diol To a solution of 2,6-dichloro-9-((3aR,4R,6aS)-2,2-dimethyltetrahydrothieno[3,4-d][1,3]dioxol-4-yl)-9H-purine, prepared in Step 1, in tetrahydrofuran (20 ml) was added 2 N HCl, followed by stirring the solution overnight. The reaction mixture was neutralized with 1 N sodium hydroxide and carefully concentrated in a vacuum. The concentrate was purified through silica gel column chromatography using a mixture of dichloromethane:methanol (20:1, v/v) as an elution solvent to afford the object compound as a white solid (1.94 g, 96%).

m.p. 198.3-200.3° C.;

UV (MeOH) λ$_{max}$ 275 nm;

$^1$H-NMR (CD$_3$OD) δ 8.87 (s, 1H), 6.08 (d, 1H, J=6.8 Hz), 4.69 (q, 1H, J=3.2 Hz), 4.48 (q, 1H, J=3.6 Hz), 3.56 (dd, 1H, J=4.4, 11.2 Hz), 2.97 (dd, 1H, J=3.4, 11.2 Hz);

[α]$^{25}_D$-50.43 (c 0.12, DMSO);

FAB-MS m/z 307 [M+H]$^+$.

Step 3. Preparation of (2R,3R,4S)-2-(2-chloro-6-(3-fluorobenzylamino)-9H-purin-9-yl)tetrahydrothiophen-3,4-diol (2R,3S,4S)-2-(2,6-dichloro-9H-purin-9-yl)tetrahydrothiophen-3,4-diol (1 equivalent), prepared in Step 2, and 3-fluorobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.10 g, 80%).

m.p. 183.2-183.5° C.;

UV (MeOH) λ$_{max}$ 275.0 nm;

$^1$H-NMR (DMSO-d$_6$) δ 8.91 (t, 1H—NH, J=5.8 Hz), 8.51 (s, 1H), 7.33-7.39 (m, 1H), 7.13-7.18 (m, 2H), 7.06 (dt, 1H, J=2.8, 11.6 Hz), 5.82 (d, 1H, J=7.2 Hz), 5.56 (d, 1H—OH, J=6.0 Hz), 5.37 (d, 1H—OH, J=4.4 Hz), 4.65 (d, 1H, J=6.0 Hz), 4.60 (m, 1H), 4.33-4.35 (m, 1H), 3.41 (dd, 1H, J=4.0, 10.8 Hz), 2.79 (dd, 1H, J=2.8, 10.8 Hz);

[α]$^{25}_D$-96.21 (c 0.12, DMSO);

FAB-MS m/z 396 [M+H]$^+$.

Example 2

Synthesis of (2R,3R,4S)-2-(2-Chloro-6-(3-chlorobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(3-chlorobenzylamino)-9H-purin-9-yl)tetrahydrothiophen-3,4-diol A procedure similar to that of Step 3 of Example 1 was conducted, with the exception that 3-chlorobenzylamine was used instead of 3-fluorobenzylamine, to give the object compound (0.11 g, 83%).

m.p. 163.3-165.3° C.;
UV (MeOH) $\lambda_{max}$ 274.5 nm;
$^1$H-NMR (CD$_3$OD) δ 8.34 (s, 1H), 7.41 (s, 1H), 7.24-7.34 (m, 3H), 5.94 (d, 1H, J=6.4 Hz), 4.75 (brs, 2H), 4.61 (q, 1H, J=3.2 Hz), 4.45 (q, 1H, J=4.0 Hz), 3.51 (dd, 1H, J=4.8, 11.2 Hz), 2.95 (dd, 1H, J=3.6, 10.8 Hz);
FAB-MS m/z 411 [M]$^+$.

Example 3

Synthesis of (2R,3R,4S)-2-(2-Chloro-6-(3-bromobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 2 was conducted to give the object compound as a white solid.

Step 3. Preparation of (2R,3R,4S)-2-(2-chloro-6-(3-bromobenzylamino)-9H-purin-9-yl)tetrahydrothiophen-3,4-diol A procedure similar to that of Step 3 of Example 1 was conducted, with the exception that 3-bromobenzylamine was used instead of 3-fluorobenzylamine, to give the object compound (0.12 g, 83%).

m.p. 184.0-185.0° C.;
UV (MeOH) $\lambda_{max}$ 274.0 nm;
$^1$H-NMR (DMSO-d$_6$) δ 8.91 (brs, 1H—NH), 8.51 (s, 1H), 7.55 (s, 1H), 7.43 (d, 1H, J=7.6 Hz), 7.33-7.35 (m, 1H), 7.26-7.30 (m, 1H), 5.82 (d, 1H, J=7.2 Hz), 5.57 (d, 1H—OH, J=6.0 Hz), 5.38 (d, 1H—OH, J=4.0 Hz), 4.60-4.63 (m, 3H), 4.34 (s, 1H), 3.41 (dd, 1H, J=4.4, 11.2 Hz), 2.80 (dd, 1H, J=2.8, 10.8 Hz);
FAB-MS m/z 456 [M+H]$^+$.

Example 4

Synthesis of (2R,3R,4S)-2-(2-Chloro-6-(3-iodobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(3-iodobenzylamino)-9H-purin-9-yl)tetrahydrothiophen-3,4-diol A procedure similar to that of Step 3 of Example 1 was conducted, with the exception that 3-iodobenzylamine was used instead of 3-fluorobenzylamine, to give the object compound (0.14 g, 84%).

m.p. 198.7-199.9° C.;
UV (MeOH) $\lambda_{max}$ 274.0 nm;
$^1$H-NMR (DMSO-d$_6$) δ 8.90 (t, 1H—NH, J=6.4 Hz), 8.51 (s, 1H), 7.74 (s, 1H), 7.60 (d, 1H, J=7.6 Hz), 7.35 (d, 1H, J=7.6 Hz), 7.13 (t, 1H, J=8.0 Hz), 5.82 (d, 1H, J=7.6 Hz), 5.56 (d, 1H, J=6.4 Hz), 5.37 (d, 1H, J=4.0 Hz), 4.60 (d, 3H, J=4.4 Hz), 4.34 (brs, 1H), 3.38 (dd, 1H, J=4.0, 10.8 Hz), 2.80 (dd, 1H, J=4.0, 10.8 Hz);
$[\alpha]^{25}_D$ -78.91 (c 0.13, DMSO);
FAB-MS m/z 504 [M+H]$^+$.

Example 5

Synthesis of (2R,3R,4S)-2-(2-Chloro-6-(2-chlorobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(2-chlorobenzylamino)-9H-purin-9-yl)tetrahydrothiophen-3,4-diol A procedure similar to that of Step 3 of Example 1, with the exception that 2-chlorobenzylamine was used instead of 3-fluorobenzylamine, was conducted to give the object compound (0.11 g, 81%).

m.p. 198.7-199.7° C.;
UV (MeOH) $\lambda_{max}$ 273.5 nm;
$^1$H-NMR (CD$_3$OD) δ 8.35 (brs, 1H), 7.45-7.47 (m, 1H), 7.39-7.43 (m, 1H), 7.25-7.29 (m, 2H), 5.95 (d, 1H, J=6.4 Hz), 4.60-4.63 (m, 1H), 4.45 (dd, 1H, J=3.6, 8.0 Hz), 3.51 (dd, 1H, J=4.8, 10.8 Hz), 2.95 (dd, 1H, J=4.0, 10.8 Hz);
$[α]^{25}_D$-96.21 (c 0.12, DMSO);
FAB-MS m/z 412 [M+H]$^+$.

Example 6

Synthesis of (2R,3R,4S)-2-(2-Chloro-6-(5-chloro-2-methoxybenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in a foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(5-chloro-2-methoxybenzylamino)-9H-purin-9-yl)tetrahydrothiophen-3,4-diol A procedure similar to that of Step 3 of Example 1 was conducted, with the exception that 5-chloro-2-methoxybenzyl amine was used instead of 3-fluorobenzylamine, to give the object compound (0.11 g, 78%).
m.p. 188.8-189.8° C.;
UV (MeOH) $\lambda_{max}$ 275.5 nm;
$^1$H-NMR (DMSO-d$_6$) δ 8.64 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.82 (d, 1H, J=7.6 Hz), 5.57 (d, 1H—OH, J=6.4 Hz), 5.37 (d, 1H—OH, J=4.0 Hz), 4.61-4.63 (m, 2H), 4.35 (m, 1H), 3.84 (s, 3H), 3.71 (dd, 1H, J=3.6, 10.4 Hz), 2.80 (dd, 1H, J=2.4, 10.8 Hz);
$[α]^{25}_D$-96.10 (c 0.21, DMSO);
FAB-MS m/z 442 [M+H]$^+$.

Example 7

Preparation of (2R,3R,4S)-2-(2-chloro-6-(2-methoxybenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in a foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(2-methoxybenzylamino)-9H-purin-9-yl)tetrahydrothiophen-3,4-diol A procedure similar to that of Step 3 of Example 1 was conducted, with the exception that 2-methoxybenzylamine was used instead of 3-fluorobenzylamine, to give the object compound (0.12 g, 88%).
m.p. 188.0° C.;
UV (MeOH) $\lambda_{max}$ 276.5 nm;
$^1$H-NMR (DMSO-d$_6$) δ 8.65 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.83 (d, 1H, J=6.8 Hz), 5.58 (d, 1H—OH, J=6.4 Hz), 5.39 (d, 1H—OH, J=3.6 Hz), 4.62-4.64 (m, 2H), 4.35 (s, 1H), 3.84 (s, 1H), 3.42 (dd, 1H, J=3.6, 10.4 Hz), 2.79-2.82 (m, 1H);
$[α]^{25}_D$- 93.53 (c 0.17, DMSO);
FAB-MS m/z 407 [M+H]$^+$.

Example 8

Synthesis of (2R,3R,4S)-2-(2-Chloro-6-(naphthalen-1-ylmethylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(naphthalen-1-ylmethylamino)-9H-purin-9-yl)tetrahydrothiophen-3,4-diol A procedure similar to that of Step 3 of Example 1 was conducted, with the exception that naphthalen-1-ylmethylamine was used instead of 3-fluorobenzylamine, to give the object compound (0.13 g, 90%).
m.p. 226.3° C. (decomp);
UV (MeOH) $\lambda_{max}$ 281.0 nm;
$^1$H-NMR (DMSO-d$_6$) δ 8.96 (t, 1H—NH, J=6.0 Hz), 8.51 (s, 1H), 8.25 (d, 1H, J=8.0 Hz), 7.95-7.97 (m, 1H), 7.83-7.85 (m, 1H), 7.53-7.61 (m, 2H), 7.43-7.46 (m, 2H), 5.82 (d, 1H, J=7.6 Hz), 5.56 (d, 1H, J=6.4 Hz), 5.38 (d, 1H, J=4.0 Hz), 5.12 (d, 1H, J=6.0 Hz), 4.59-4.61 (m, 1H), 4.34-4.35 (m, 1H), 3.40-3.44 (m, 1H), 2.80 (dd, 1H, J=2.4, 6.8 Hz);
FAB-MS m/z 428 [M+H]$^+$.
UV (MeOH) $\lambda_{max}$ 281.0 nm;
$^1$H-NMR (DMSO-d$_6$) δ 8.96 (t, 1H—NH, J=6.0 Hz), 8.51 (s, 1H), 8.25 (d, 1H, J=8.0 Hz), 7.95-7.97 (m, 1H), 7.83-7.85 (m, 1H), 7.53-7.61 (m, 2H), 7.43-7.46 (m, 2H), 5.82 (d, 1H, J=7.6 Hz), 5.56 (d, 1H, J=6.4 Hz), 5.38 (d, 1H, J=4.0 Hz), 5.12 (d, 1H, J=6.0 Hz), 4.59-4.61 (m, 1H), 4.34-4.35 (m, 1H), 3.40-3.44 (m, 1H), 2.80 (dd, 1H, J=2.4, 6.8 Hz);
FAB-MS m/z 428 [M+H]$^+$.

Example 9

Synthesis of 3-((2-chloro-9-((2R,3R,4S)-3,4-dihydroxytetrahydrothiophen-2-yl)-9H-purine-6-ylamino)methyl)benzoic acid

Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of 3-((2-chloro-9-((2R,3R,4S)-3,4-dihydroxytetrahydrothiophen-2-yl)-9H-purine-6-ylamino)methyl)benzoic acid A procedure similar to that of Step 3 of Example 1 was conducted, with the exception that 3-(aminomethyl)benzoic acid was used instead of 3-fluorobenzylamine, to give the object compound (0.12 g, 84%).

mp 254.0-256.99° C.;
UV (MeOH) $\lambda_{max}$ 275.5 nm;
$^1$H-NMR (DMSO-$d_6$) δ 8.95 (t, 1H—NH, J=6.0 Hz), 8.52 (s, 1H), 7.89 (d, 1H, J=8.4 Hz), 7.43 (d, 1H, J=8.0 Hz), 5.82 (d, 1H, J=7.6 Hz), 5.57 (brs, 1H), 5.38 (brs, 1H), 4.71 (d, 1H, J=6.0 Hz), 4.60 (brs, 1H), 4.34 (brs, 1H), 3.41 (dd, 1H, J=4.0, 10.8 Hz), 2.80 (dd, 1H, J=2.8, 10.8 Hz);
$[\alpha]^2_D$-94.55 (c 0.11, DMSO);
FAB-MS m/z 422 [M+H]$^+$.

Example 10

Synthesis of 2-(2-Chloro-6-methylamino-purin-9-yl) (2R,3S,4R)-tetrahydrothiophen-3,4-diol

Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of 2-(2-chloro-6-methylamino-purin-9-yl) (2R,3S,4R)-tetrahydrothiophen-3,4-diol A procedure similar to that of Step 3 of Example 1 was conducted, with the exception that methylamine was used instead of 3-fluorobenzylamine, to give the object compound (0.89 g, 90%).

UV (MeOH) $\lambda_{max}$ 269.5 nm (pH 7);
$^1$H-NMR (CDCl$_3$) δ 2.99 (1H, dd, 4'-CH, J=4.4, 10.8 Hz), 3.12 (3H, brs, NH—CH$_3$), 3.44 1H, dd, 4'-CH, J=4, 10.8 Hz), 4.41 (1H, m, 2'-CH, J=5.6 Hz), 4.47 (1H, m, 3'-CH), 5.89 (1H, d, 1'-CH, J=5.6 Hz), 8.40 (s, 1H, 8-CH);
$[\alpha]^{25}_D$-34.8 (c 0.115, DMSO);
FAB-MS m/z 302.3 [M+H]$^+$.

Example 11

Synthesis of (2R,3R,4S)-2-(6-(3-fluorobenzylamino)-9H-purin-9-yl)tetrahydrothiophen-3,4-diol

Step 1. Preparation of 6-chloro-9-((3aR,4R,6aS)-2,2-dimethyltetrahydrothieno[3,4-d][1,3]dioxol-4-yl)-9H-purine A procedure similar to that of Step 1 of Example 1 was conducted, with the exception that 6-chloropurine (2.29 g, 22.12 mmol) was used instead of 2,6-chloropurine, to give the object compound in foam form (1.84 g, 91%).

UV (CH$_2$Cl$_2$) $\lambda_{max}$ 265.0 nm;
$^1$H-NMR (CDCl$_3$) δ 8.67 (pseudo t, 1H, J=1.4 Hz), 8.23 (s, 1H), 5.88 (s, 1H), 5.23 (m, 2H), 3.69 (dd, 1H, J=4.0, 13.2 Hz), 3.18 (d, 1H, J=12.8 Hz), 1.52 (s, 3H), 1.29 (s, 3H);
$^{13}$C-NMR (CDCl$_3$) δ 152.05, 151.39, 151.09, 144.34, 132.56, 111.90, 89.60, 84.31, 70.30, 40.76, 26.40, 24.63;
$[\alpha]^{25}_D$-157.64 (c 0.15, MeOH);
FAB-MS m/z 313 [M+H]$^+$.

Step 2. Preparation of (2R,3S,4S)-2-(6-chloro-9H-purin-9-yl)tetrahydrothiophen-3,4-diol Synthesis was conducted from 6-chloro-9-((3aR,4R,6aS)-2,2-dimethyltetrahydrothieno[3,4-d][1,3]dioxol-4-yl)-9H-purine (1.84 g, 5.88 mmol), prepared in Step 1, in a manner similar to that of Step 2 of Example 1 to afford the object compound as a white solid (1.27 g, 79%).

m.p. 192.3-192.8° C.;
UV (MeOH) A 264.5 nm;
$^1$H-NMR (DMSO-$d_6$) δ 9.02 (s, 1H), 8.82 (s, 1H), 6.02 (d, 1H, J=7.6 Hz), 5.62 (d, 1H—OH, J=6.0 Hz), 5.43 (d, 1H—OH, J=4.0 Hz), 4.70-4.74 (m, 1H), 4.36-4.40 (m, 1H), 3.47 (dd, 1H, J=4.0, 10.8 Hz), 3.17 (d, 1H, J=5.2 Hz), 2.84 (dd, 1H, J=2.8, 11.2 Hz);
$[\alpha]^{25}_D$-109.15 (c 0.16, DMSO);
FAB-MS m/z 273 [M+H]$^+$.

Step 3. Preparation of (2R,3R,4S)-2-(6-(3-fluorobenzylamino)-9H-purin-9-yl)tetrahydrothiophen-3,4-diol (2R,3S,4S)-2-(6-chloro-9H-purin-9-yl)tetrahydrothiophen-3,4-diol (1 equivalent), prepared in Step 2, and 3-fluorobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.11 g, 82%).

m.p. 180.5-180.7° C.;
UV (MeOH) A. 273.5 nm;
$^1$H-NMR (DMSO-$d_6$) δ 8.46 (s, 1H), 8.22 (s, 1H), 7.31-7.39 (m, 1H), 7.12-7.18 (m, 2H), 7.01-7.05 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1H), 3.39-3.43 (m, 1H), 3.17 (d, 1H, J=5.2 Hz), 2.80 (dd, 1H, J=3.2, 11.2 Hz);
$[\alpha]^{25}_D$-141.2 (c 0.11, DMSO);
FAB-MS m/z 362 [M+H]$^+$.

Example 12

Synthesis of (2R,3R,4S)-2-(6-(3-Chlorobenzylamino)-9H-purin-9-yl)tetrahydrothiophen-3,4-diol

Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-chlorobenzylamino)-9H-purin-9-yl)tetrahydrothiophen-3,4-diol A procedure similar to that of Step 3 of Example 11 was conducted, with the exception that 3-chlorobenzylamine was used instead of 3-fluorobenzylamine, to give the object compound (0.12 g, 85%).

m.p. 165.0-165.3° C.;
UV (MeOH) $\lambda_{max}$ 274.5 nm;
$^1$H-NMR (DMSO-d$_6$) δ 8.47 (s, 1H), 8.22 (s, 1H), 7.39 (s, 1H), 7.26-7.35 (m, 3H), 5.91 (d, 1H, J=7.2 Hz), 5.53 (d, 1H—OH, J=6.4 Hz), 5.35 (d, 1H—OH, J=4.0 Hz), 4.67-4.71 (m, 2H), 4.33-4.37 (m, 1H), 3.40-3.48 (m, 2H), 2.80 (dd, 1H, J=3.2, 10.4 Hz);
$[\alpha]^{25}_D$-162.5 (c 0.10, DMSO);
FAB-MS m/z 378 [M+H]$^+$.

Example 13

Synthesis of (2R,3R,4S)-2-(6-(3-bromobenzylamino)-9H-purin-9-yl)tetrahydrothiophen-3,4-diol

Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-bromobenzylamino)-9H-purin-9-yl)tetrahydrothiophen-3,4-diol A procedure similar to that of Step 3 of Example 11 was conducted, with the exception that 3-bromobenzylamine was used instead of 3-fluorobenzylamine, to give the object compound (0.11 g, 70%).

m.p. 183.0-184.0° C.;
UV (MeOH) $\lambda_{max}$ 270.0 nm;
$^1$H-NMR (DMSO-d$_6$) δ 8.46 (s, 1H), 8.22 (s, 1H), 7.53 (s, 1H), 7.39-7.42 (m, 1H), 7.34-7.35 (m, 1H), 7.24-7.28 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1 H), 3.41 (dd, 1H, J=4.0, 10.8 Hz), 3.06 (q, 1H, J=7.2 Hz), 2.80 (dd, 1H, J=2.8, 10.8 Hz);
$[\alpha]^{25}_D$-100.72 (c 0.14, DMSO);
FAB-MS m/z 422 [M+H]$^+$.

Example 14

Synthesis of (2R,3R,4S)-2-(6-(3-Iodobenzylamino)-9H-purin-9-yl)tetrahydrothiophen-3,4-diol

Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-iodobenzylamino)-9H-purin-9-yl)tetrahydrothiophen-3,4-diol A procedure similar to that of Step 3 of Example 11 was conducted, with the exception that 3-iodobenzylamine was used instead of 3-fluorobenzylamine, to give the object compound (0.12 g, 72%).

m.p. 198.8-199.8° C.;
UV (MeOH) $\lambda_{max}$ 271.5 nm;
$^1$H-NMR (DMSO-d$_6$) δ 8.46 (s, 1H), 8.22 (s, 1H), 7.72 (s, 1H), 7.56-7.59 (m, 1H), 7.35-7.36 (d, 1H, J=7.6 Hz), 7.01-7.12 (m, 1H), 5.90 (d, 1H, J=7.2 Hz), 5.53 (d, 1H—OH, J=6.4 Hz), 5.35 (d, 1H—OH, J=4.4 Hz), 4.67-4.71 (m, 2H), 4.34-4.38 (m, 1H), 3.41 (dd, 1H, J=4.0, 10.8 Hz), 3.16 (d, 1H, J=7.2 Hz), 2.80 (dd, 1H, J=2.8, 10.8 Hz);
$[\alpha]^{25}_D$-97.08 (c 0.14, DMSO);
FAB-MS m/z 470 [M+H]$^+$.

Example 15

Synthesis of (2R,3R,4R)-2-(6-(3-Bromobenzylamino)-2-chloro-9H-purin-9-yl)tetrahydrofuran-3,4-diol

Step 1. Preparation of 2,6-dichloro-9-((3aR,4R,6aR)-2,2-dimethyltetrahydrofuro[3,4-d][1,3]dioxol-4-yl)-9H-purine Synthesis was conducted using (3aR,4R,6aR)-2,2-dimethyltetrahydrofuro[3,4-d][1,3]dioxol-4-ol (702.1 g, 3.472 mmol), prepared in Preparation Example 2, in the same manner as in Step 1 of Example 1 to afford the object compound in foam form (793.0 mg, 69%).

UV (MeOH) $\lambda_{max}$ 276.5 nm;
$^1$H-NMR (CDCl$_3$) δ 8.15 (s, 1H), 6.07 (s, 1H), 5.41 (d, 1H, J=6.0 Hz), 5.26-5.29 (m, 1H), 4.25-4.31 (m, 2H), 1.57 (s, 3H), 1.41 (s, 3H);
$[\alpha]^{25}_D$-21.00 (c 0.10, DMSO);
FAB-MS m/z 331 [M+H]$^+$.

Step 2. Preparation of (2R,3R,4R)-2-(2,6-dichloro-9H-purin-9-yl)tetrahydrofuro-3,4-diol Synthesis was conducted using 2,6-dichloro-9-((3aR,4R,6aS)-2,2-dimethyltetrahydrofuro[3,4-d][1,3]dioxol-4-yl)-

9H-purine (900 mg, 2.0 mmol), prepared in Step 1, in the same manner as in Step 2 of Example 1 to give the object compound as a white solid (0.46 g, 80%).

m.p. 122.7-123.4° C.;
UV (MeOH) $\lambda_{max}$ 276.5 nm;
$^1$H-NMR (DMSO-d$_6$) δ 8.98 (s, 1H), 5.96 (d, 1H, J=6.4 Hz), 5.57 (d, 1H—OH, J=6.0 Hz), 5.32 (d, 1H—OH, J=4.0 Hz), 4.69-4.74 (m, 1H), 4.41 (dd, 1H, J=3.6, 9.2 Hz), 4.29-4.32 (m, 1H), 3.87 (dd, 1H, J=2.0, 9.6 Hz);
$[\alpha]^{25}_D$-68.09 (c 0.14, DMSO);
FAB-MS m/z 291 [M+H]$^+$.

Step 3. Preparation of (2R,3R,4R)-2-(6-(3-bromobenzylamino)-2-chloro-9H-purin-9-yl)tetrahydrofuro-3,4-diol (2R,3S,4S)-2-(2,6-dichloro-9H-purin-9-yl)tetrahydrofuro-3,4-diol (1 equivalent), prepared in Step 2, and 3-bromobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.12 g, 82%).

m.p. 181.5-181.7° C.;
UV (MeOH) $\lambda_{max}$ 274.5 nm;
$^1$H-NMR (DMSO-d$_6$) δ 8.92 (t, 1H—NH, J=6.0 Hz), 8.43 (S, 1H), 7.55 (s, 1H), 7.44 (d, 1H, J=8.0 Hz), 7.33-7.35 (m, 1H), 7.26-7.30 (m, 1H), 5.81 (d, 1H, J=6.4 Hz), 5.47 (d, 1H, J=6.4 Hz), 5.22 (d, 1H, J=4.0 Hz), 4.66-4.69 (m, 1H), 4.62 (s, 2H), 4.32 (dd, 1H, J=3.6, 9.2 Hz), 4.25 (brs, 1H), 3.80 (dd, 1H, J=1.6, 9.2 Hz);
$[\alpha]^{25}_D$-62.75 (c 0.10, DMSO);
FAB-MS m/z 440 [M+H]$^+$.

Example 16

Synthesis of (2R,3R,4R)-2-(6-(3-iodobenzylamino)-2-chloro-9H-purin-9-yl)tetrahydrofuro-3,4-diol Step 1. Preparation of 2,6-dichloro-9-((3aR,4R,6aR)-2,2-dimethyltetrahydrofuro[3,4-d][1,3]dioxol-4-yl)-9H-purine The same procedure as in Step 1 of Example 15 was conducted to give the object compound in foam form.

Step 2. Preparation of (2R,3R,4R)-2-(2,6-dichloro-9H-purin-9-yl)tetrahydrofuro-3,4-diol The same procedure as in Step 2 of Example 15 was conducted to give the object compound as a white solid in syrup form.

Step 3. Preparation of (2R,3R,4R)-2-(6-(3-iodobenzylamino)-2-chloro-9H-purin-9-yl)tetrahydrofuro-3,4-diol A procedure similar to that of Step 3 of Example 15 was conducted, with the exception that 3-iodobenzylamine was used instead of 3-bromobenzylamine to give the object compound (0.13 g, 78%).

m.p. 195.5-195.8° C.;
UV (MeOH) $\lambda_{max}$ 274.0 nm;
$^1$H-NMR (DMSO-d$_6$) δ 8.91 (t, 1H—NH, J=6.4 Hz), 8.44 (s, 1H), 7.75 (s, 1H), 7.61 (d, 1H, J=8.0 Hz), 7.36 (d, 1H, J=7.6 Hz), 7.13 (t, 1H, J=4.0 Hz), 5.81 (d, 1H, J=6.8 Hz), 5.47 (d, 1H—OH, J=6.8 Hz), 5.23 (d, 1H—OH, J=4.0 Hz), 4.72 (dd, 1H, J=6.4, 10.8 Hz), 4.61 (d, 1H, J=6.0 Hz), 4.34 (dd, 1H, J=3.6, 9.2 Hz), 3.81 (dd, 1H, J=1.2, 9.2 Hz);
$[\alpha]^{25}_D$-68.07 (c 0.12, DMSO);
FAB-MS m/z 488 [M+H]$^+$.

Experimental Example 1

Assay for Binding Affinity for Adenosine Receptors

The adenosine derivatives of the present invention were assayed for binding affinity for human $A_1$, $A_{2A}$ and $A_3$ adenosine receptors as follows.

CHO cells (ATCC No. CCL-61), in which $A_1$ and $A_3$ adenosine receptors were expressed, were cultured in F-12 media (Gibco, U.S.A.) supplemented with 10% fetal bovine serum (FBS) and penicillin/streptomycin (100 units/ml and 100 μg/ml), at 37° C. in a 5% $CO_2$ atmosphere. A predetermined amount of suitable hAR-expressed CHO cells was mixed with labeled ligands (1 nM [$^3$H]CCPA and 0.5 nM [$^{125}$I]AB-MECA) specifically binding to $A_1$ and $A_3$ adenosine receptors in a 50/10/1 buffer in test tubes. The derivatives of the present invention were dissolved at various concentrations in dimethylsulfoxide (DMSO) and diluted in the buffer, taking care that the final concentration of DMSO did not exceed 1%. Incubation for 1 hr in a 37° C. incubator was followed by rapid filtration in a vacuum using a cell collector (TOMTEC, U.S.A.). Subsequently, the test tubes were washed three times with 3 ml of the buffer before radioactivity was measured using a γ-counter. In the same condition as that for total binding, the equilibrium constant $K_i$ for non-specific binding was determined in the presence of 10 μM of 5'-N-ethylcarboxamide adenosine (NECA) as a non-labeled ligand. The equilibrium constant $K_i$ was calculated according to the Cheng-Prusoff equation on the assumption that [$^{125}$I] AB-MECA has a $K_d$ value of 1.48 nM. $K_i$ for binding affinity was determined by subtracting the non-specific binding value from the total binding value. On the basis of the specific binding values, the samples were analyzed for binding affinity to various adenosine receptors.

In addition, the binding of the labeled ligand [$^3$H]CGS-21680 (2-(((4-(2-carboxyethyl)phenyl)ethylamino)-5'-N-ethylcarbamoyl)adenosine) to the $A_{2A}$ adenosine receptor expressed on HEK 293 cell was assayed as follows. Adenosine deaminase was added alone or in combination with a radioactive ligand when cerebral meninges were incubated at 30° C. for 30 min. Each of the compounds synthesized in the examples was measured for IC$_{50}$ at least 6 different concentrations, and the measurements were analyzed using PLAT? software to determine $K_i$ values. Chemical Structures of the compounds synthesized in the examples, substitutents, and $K_1$ values for binding affinity are summarized in Table 1, below.

TABLE 1

| Ex. No. | Structures | Substituents | | | $K_i$ (nM) or % | | |
|---|---|---|---|---|---|---|---|
| | | A | R | Y | $hA_1$ | $hA_{2A}$ | $hA_3$ |
| 1 | | S | 3-fluorobenzyl | Cl | 19.8% | 47.6% | 7.4 ± 1.3 |
| 2 | | S | 3-chlorobenzyl | Cl | 37.9% | 17.7% | 1.66 ± 0.90 |
| 3 | | S | 3-bromobenzyl | Cl | 34.2% | 18.4% | 8.99 ± 5.17 |
| 4 | | S | 3-iodobenzyl | Cl | 2490 ± 940 | 341 ± 75 | 4.16 ± 0.50 |

TABLE 1-continued

| Ex. No. | Structures | Substituents | | | $K_1$ (nM) or % | | |
|---|---|---|---|---|---|---|---|
| | | A | R | Y | $hA_1$ | $hA_{2A}$ | $hA_3$ |
| 5 | 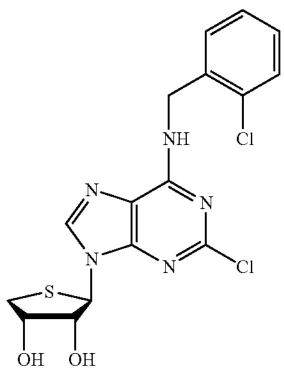 | S | 2-chlorobenzyl | Cl | 12.8% | 1600 ± 135 | 25.8 ± 6.3 |
| 6 | 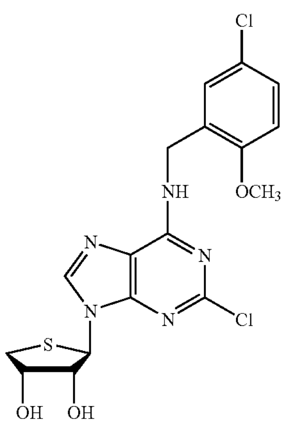 | S | 5-chloro-2-methoxybenzyl | Cl | 23.8% | 4020 ± 1750 | 12.7 ± 3.7 |
| 7 | 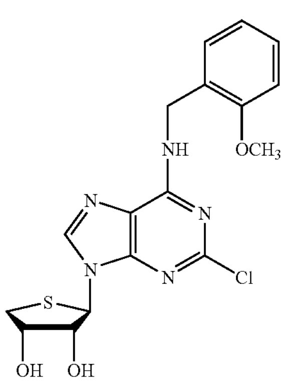 | S | 2-methoxybenzyl | Cl | 9.4% | 17.5% | 19.9 ± 7.1 |

TABLE 1-continued

| Ex. No. | Structures | Substituents | | | $K_i$ (nM) or % | | |
|---|---|---|---|---|---|---|---|
| | | A | R | Y | $hA_1$ | $hA_{2A}$ | $hA_3$ |
| 8 | | S | 1-naphthylmethyl | Cl | 22.0% | −8.3% | 24.8 ± 8.1 |
| 9 | | S | 3-toluic acid | Cl | 13.1% | −0.18% | 41.5% |
| 10 | | S | methyl | Cl | 55.4 ± 1.8% | 45.0 ± 1.4% | 3.69 ± 0.25 |
| 11 | | S | 3-fluorobenzyl | H | 1430 ± 420 | 1260 ± 330 | 7.3 ± 0.6 |

TABLE 1-continued

| Ex. No. | Structures | A | R | Y | hA$_1$ | hA$_{2A}$ | hA$_3$ |
|---|---|---|---|---|---|---|---|
| 12 | (structure) | S | 3-chlorobenzyl | H | 860 ± 210 | 440 ± 110 | 1.5 ± 0.4 |
| 13 | (structure) | S | 3-bromobenzyl | H | 790 ± 190 | 420 ± 32 | 6.8 ± 3.4 |
| 14 | (structure) | S | 3-iodobenzyl | H | 530 ± 97 | 230 ± 65 | 2.5 ± 1.0 |
| 15 | (structure) | O | 3-bromobenzyl | Cl | 39.8% | 22.8% | 13.0 ± 6.9 |

TABLE 1-continued

| Ex. No. | Structures | Substituents | | | K₁ (nM) or % | | |
|---|---|---|---|---|---|---|---|
| | | A | R | Y | $hA_1$ | $hA_{2A}$ | $hA_3$ |
| 16 | 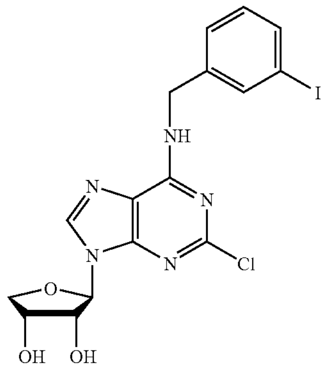 | O | 3-iodobenzyl | Cl | 37.7% | 28.6% | 42.9 ± 8.9 |

Unit: nM ± SEM
"%" represents percentage inhibition of specific binding of 10 μM labeled ligand in the presence of 10 μM of the unlabeled ligand NECA.

As can be understood from the data of Table 1, the compounds synthesized in the examples of the present invention were found to have high binding affinity for human $A_3$ adenosine receptors ($hA_3$ AR), but low affinity for $A_1$ and $A_{2A}$ adenosine receptors, thereby showing high selectivity. Particularly, the compound of Example 12 shows the highest binding affinity for $hA_3$ AR, with $K_i$ determined to be 1.50±0.40 nM, followed by the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM) in decreasing order of binding affinity. Also, the compound of Example 4 was measured to have high binding affinity for the rat $A_3$ adenosine receptor expressed in CHO cells ($K_i$=3.89±1.15 nM) and was not observed as an agonist or antagonist on human $A_{2B}$ adenosine receptor.

In addition, the compounds having halobenzoyl substituents were found to have binding affinity in decreasing order of Cl>I>F>Br. The compound of Example 2, having 3-chlorobenzyl, had higher binding affinity for $hA_3$ adenosine receptor than the compound of Example 5, having 2-chlorobenzyl ($K_i$=25.8±6.3 nM). In addition, the adenosine derivatives having a substituent at the 3-position of the benzene ring in accordance with the present invention had stronger binding affinity for $hA_3$ AR than the adenosine derivatives, having a substituent at the 2- or 4-position, or two substituents at the 2- and 5-position. The compounds of Examples 15 and 16, both adenosine derivatives having 4'-O oxonucleoside forms, also had high binding affinity and selectivity, which were, however, not superior to those of the corresponding 4'-S thionucleoside forms, such as those of Examples 3 and 4. The compounds of Examples 10 to 14, in which the chloro group at the 2-position of the purine base was substituted with a hydrogen atom, were observed to exceed the 2-chloro compounds with regard to binding affinity and selectivity.

Experimental Example 2

Antagonist Effect of Adenosine Derivatives on $A_3$ Adenosine Receptors and cAMP Inhibition In order to examine whether the derivatives of the present invention are effective as human $A_3$ adenosine receptor antagonists, an assay for antagonism and cAMP inhibition was conducted by treating CHO cells with the compound of Example 4 and Cl-IB-MECA.

When CHO cells, in which human $A_3$ adenosine receptor was expressed, were treated with various concentrations of the compound of Example 4, as seen in FIG. 1, the agonist effect of the 100% pure agonist Cl-IB-MECA was observed to be inhibited in a dose-dependent manner, indicating that the compound of the present invention competes with Cl-IB-MECA for the same receptor binding site. Results of a test for human $A_3$ adenosine receptor-mediated cAMP inhibition in the CHO cells demonstrates that the compounds synthesized in the examples of the present invention are 100% pure $A_3$ adenosine receptor antagonists. Thus, the compounds synthesized according to the present invention are found to exhibit a dissociation constant $K_B$ of 1.92 nM, as measured using Schild analysis.

Experimental Examples 3 to 6

Anti-Inflammatory Activity of Adenosine Derivatives

The adenosine derivatives of the present invention were examined for anti-inflammatory activity in the following animal test. Seven-week-old male ICR mice were treated with TPA (12-O-tetradecanoylphorbol 13-acetate, 20 μl) in the right ear. Within 15 minutes, the compounds of Examples 1 to 16 were diluted at a concentration of 0.5% in acetone (20 μl), distilled water, or mixtures of DMSO and acetone (compositions shown in Tables 2 to 5) before being administered to the mice. Hydrocortisone was used at the same concentration as a control.

6 hrs after treatment with TPA, the mice were secondarily treated with the adenosine derivatives of the present invention. 24 hrs after TPA treatment, test animals were euthanized using a cervical dislocation method. Samples were obtained from the right ear using a 6 mm diameter punch. The activity was observed by measuring the ear sample using a microbalance. Percentages of inhibition were calculated using the following Equation 1. The compositions and amounts used in these experiments are summarized in Tables 2 to 5 and the anti-inflammatory activities thereof are shown in FIGS. 2 to 5.

$$\% \text{ Inhibition} = \frac{1 - Rt.Ear(\text{Test-Non treated})}{Rt.Ear(\text{TPA only-Non treated})} \quad \text{[Equation 1]}$$

TABLE 2

| Exp. Ex. 3 | Compositions | Amounts |
|---|---|---|
| 3-1 | Non-treated | — |
| 3-2 | TPA alone | 20 μl |
| 3-3 | TPA + acetone | 20 μl + 20 μl |
| 3-4 | TPA + acetone + Cpd. Of Ex. 2 | 20 μl + 0.5%/20 μl |
| 3-5 | TPA + acetone + Cpd. Of Ex. 3 | 20 μl + 0.5%/20 μl |
| 3-6 | TPA + acetone + Cpd. Of Ex. 4 | 20 μl + 0.5%/20 μl |
| 3-7 | TPA + acetone + hydrocortisone | 20 μl + 0.5%/20 μl |

TABLE 3

| Exp. Ex. 4 | Compositions | Amounts |
|---|---|---|
| 4-1 | Non-treated | — |
| 4-2 | TPA alone | 20 μl |
| 4-3 | TPA + acetone | 20 μl + 20 μl |
| 4-4 | TPA + acetone + Cpd. Of Ex. 1 | 20 μl + 0.5%/20 μl |
| 4-5 | TPA + acetone + Cpd. Of Ex. 6 | 20 μl + 0.5%/20 μl |
| 4-6 | TPA + acetone + hydrocortisone | 20 μl + 0.5%/20 μl |

TABLE 4

| Exp. Ex. 5 | Compositions | Amounts |
|---|---|---|
| 5-1 | Non-treated | — |
| 5-2 | TPA alone | 20 μl |
| 5-3 | TPA + solvent mix (water:acetone 1:4) | 20 μl + 20 μl |
| 5-4 | TPA + solvent mix + Cpd. Of Ex. 5 | 20 μl + 0.5%/20 μl |
| 5-5 | TPA + solvent mix + Cpd. Of Ex. 7 | 20 μl + 0.5%/20 μl |
| 5-6 | TPA + solvent mix + Cpd. Of Ex. 8 | 20 μl + 0.5%/20 μl |
| 5-7 | TPA + solvent mix + hydrocortisone | 20 μl + 0.5%/20 μl |

TABLE 5

| Exp. Ex. 6 | Compositions | Amounts |
|---|---|---|
| 6-1 | Non-treated | — |
| 6-2 | TPA alone | 20 μl |
| 6-3 | TPA + solvent mix (DMSO:acetone 1:9) | 20 μl + 20 μl |
| 6-4 | TPA + solvent mix + Cpd. Of Ex. 15 | 20 μl + 0.5%/20 μl |
| 6-5 | TPA + solvent mix + Cpd. Of Ex. 16 | 20 μl + 0.5%/20 μl |
| 6-6 | TPA + solvent mix + hydrocortisone | 20 μl + 0.5%/20 μl |

Figure 2:
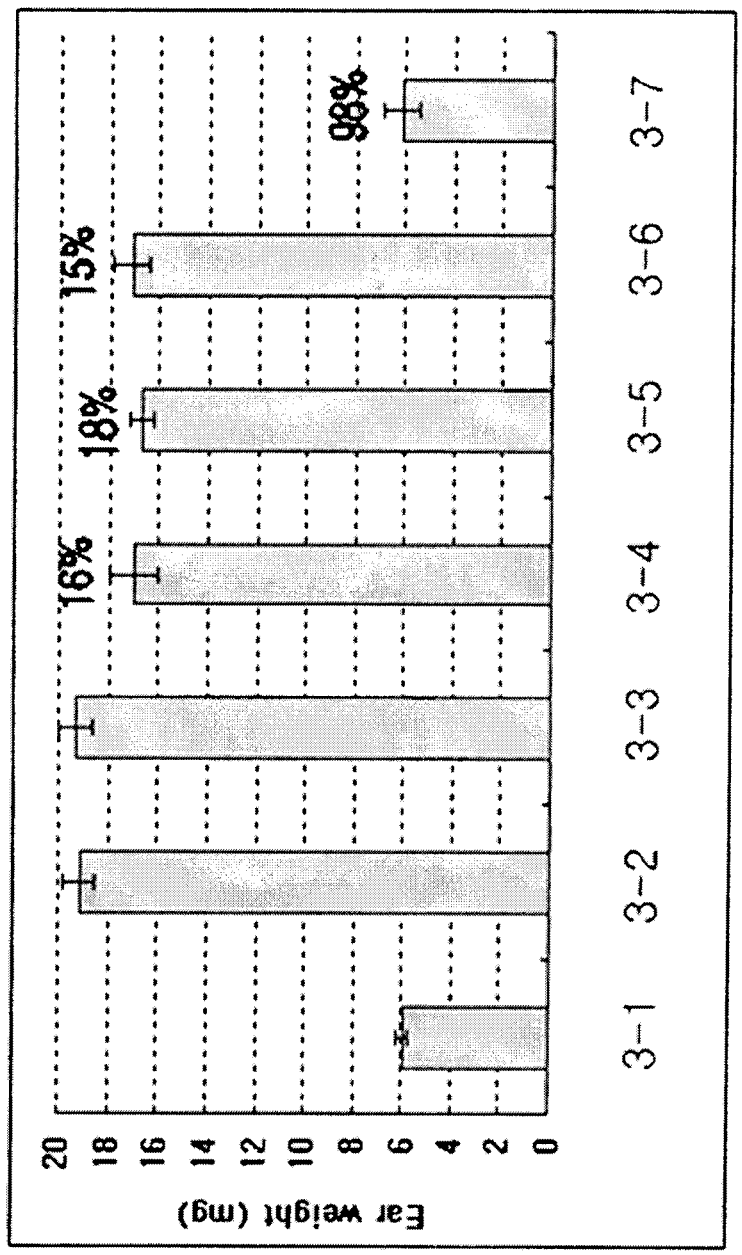
FIG. 2 is a graph showing the anti-inflammatory activity of the compounds of the present invention (Examples 2, 3 and 4) in animal tests.

When applied to the mice, as seen in FIG. 2, dilutions of the compounds of Examples 2 to 4 were found to inhibit the TPA-induced inflammation of the mouse ear to some degree, although this anti-inflammatory activity was very small compared to that of the control hydrocortisone.

Figure 3:
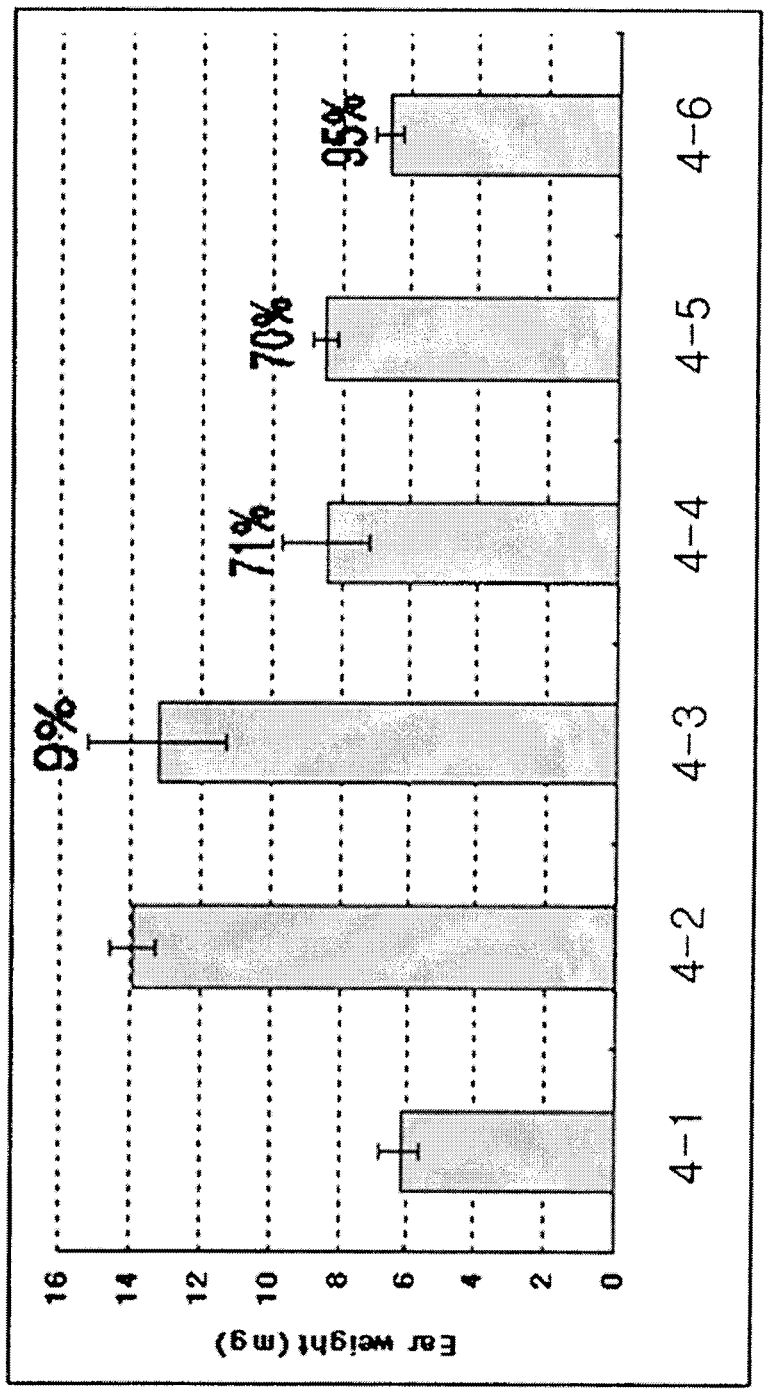
FIG. 3 is a graph showing the anti-inflammatory activity of the compounds of the present invention (Examples 1 and 6) in animal tests.

The anti-inflammatory activity of the compounds of Examples 1 and 6, as shown in FIG. 3, was measured to be four or more times that of the compounds of Examples 2 to 4.

As seen in FIG. 4, the compounds of Examples 5, 7 and 8, diluted at a concentration of 0.5% in a mixture of distilled water and acetone (1:4), were measured to have percentages of inflammation inhibition of 17%, 34% and 53%, respectively.

As shown in FIG. 5, the compounds of Examples 15 and 16, diluted at a concentration of 0.5% in a mixture of DMSO and acetone (1:9), were measured to have percentages of inflammation inhibition of 59% and 79%, respectively. Based on the observations in this test, the adenosine derivatives of the present invention were proven to have anti-inflammatory activity.

Experimental Example 7

Toxicity Assay

The compounds synthesized in the examples of the present invention were assayed for cytotoxicity in animals. Three test groups of three 25±5 g ICR rats (Central Experiment Animal, Korea) and three test groups of three 235±10 g specific pathogen-free (SPF) Sprague Dawley rats (Central Experiment Animal, Korea) were abdominally administered with the compound of Example 2 at doses of 20 mg/kg, 10 mg/kg, and 1 mg/kg, respectively, followed by observation for 24 hrs.

None of the members of the three groups died. No difference in weight gain or feed intake was detected between the control group and the test groups. Therefore, the derivative compounds of the present invention were proven as being safe.

The adenosine compounds of the present invention may be administered in the following dosage forms and the following Formulation Examples are set forth to illustrate, but not limit, the present invention.

<FORMULATION EXAMPLE 1> Preparation of Powder

| Adenosine Derivative | 500 mg |
|---|---|
| Corn Starch | 100 mg |
| Lactose | 100 mg |
| Talc | 10 mg |

The ingredients were mixed and filled in an airtight bag.

<FORMULATION EXAMPLE 2> Preparation of Tablet

| Adenosine Derivative | 100 mg |
|---|---|
| Corn Starch | 100 mg |
| Lactose | 100 mg |
| Mg Stearate | 2 mg |

The ingredients were mixed and compressed into tablets according to a conventional method.

<FORMULATION EXAMPLE 3> Preparation of Capsule

| Adenosine Derivative | 50 mg |
|---|---|
| Lactose | 50 mg |
| Mg Stearate | 1 mg |

The ingredients were mixed and filled in gelatin capsules according to a conventional method.

<FORMULATION EXAMPLE 4> Preparation of Injection

| Adenosine Derivative | 10 mg |
|---|---|
| Sterile Water for injection | suitable amount |
| pH Adjuster | Suitable amount |

The pH of a solution of the active ingredient in distilled water was adjusted to 7.5 and the solution was diluted in sterile water to a volume 2 ml and loaded into ampules before sterilization.

<FORMULATION EXAMPLE 5> Preparation of Liquid Form

| | |
|---|---|
| Adenosine Derivative | 1 g |
| Isomerized Sugar | 10 g |
| Sucrose | 10 g |
| Lemon Flavor | suitable amount |
| Pure water | suitable amount |

A liquid dosage form was prepared by dissolving the ingredients in pure water, adding a suitable amount of lemon flavor, increasing the volume to 100 ml with pure water, loading the volume into a brown vial, and sterilizing.

INDUSTRIAL APPLICABILITY

As described hitherto, the adenosine derivatives of the present invention have high binding affinity and selectivity for adenosine receptors, especially for $A_3$ adenosine receptors, and act as $A_3$ adenosine receptor antagonists, showing anti-inflammatory activity. Therefore, the adenosine derivatives of the present invention are useful in the prevention and treatment of inflammatory diseases.

Examples are described in terms of the preferred embodiment of present invention. However, it should not be understood that such disclosure is not limited to explicit description of present invention. The description and the claims of present invention are to be interpreted as covering all alterations and modifications within the true scope of this invention.

The invention claimed is:

1. A method for synthesizing an $A_3$ adenosine receptor antagonist, comprising a (2R,3R,4S) tetrahydrothiophen based adenosine derivative or a pharmaceutically acceptable salt thereof, the method comprising:
   (1) reacting a starting material of Chemical formula 2 with a silylated purine derivative of Chemical formula 5 in the presence of a Lewis acid as a catalyst to give a β-anomer to give a compound of Chemical formula 3;
   (2) adding HCl to the compound of Chemical formula 3 obtained in (1) to give a diol compound 4 of Chemical formula 4; and
   (3) reacting the diol compound of Chemical formula 4 obtained in (2) with an amine compound in the presence of a base as a catalyst to give the $A_3$ adenosine receptor antagonist, wherein the (2R,3R,4S) tetrahydrothiophen based adenosine derivative is selected from the group consisting of:
   (2R,3R,4S)-2-(2-chloro-6-(3-fluorobenzylamino)-9H-purin-9-yl)tetrahydrothiophen-3,4-diol,
   (2R,3R,4S)-2-(2-chloro-6-(3-chlorobenzylamino)-9H-purin-9-yl)tetrahydrothiophen-3,4-diol,
   (2R,3R,4S)-2-(6-(3-bromobenzylamino)-2-chloro-9H-purin-9-yl)tetrahydrothiophen-3,4-diol,
   (2R,3R,4S)-2-(2-chloro-6-(3-iodobenzylamino)-9H-purin-9-yl)tetrahydrothiophen-3,4-diol,
   (2R,3R,4S)-2-(2-chloro-6-(2-chlorobenzylamino)-9H-purin-9-yl)tetrahydrothiophen-3,4-diol,
   (2R,3R,4S)-2-(2-chloro-6-(5-chloro-2-methoxybenzylamino)-9H-purin-9-yl)tetrahydrothiophen-3,4-diol,
   (2R,3R,4S)-2-(2-chloro-6-(2-methoxybenzylamino)-9H-purin-9-yl)tetrahydrothiophen-3,4-diol,
   (2R,3R,4S)-2-(2-chloro-6-(naphthalen-1-ylmethylamino)-9H-purin-9-yl)tetrahydrothiophen-3,4-diol,
   3-((2-chloro-9-((2R,3R,4S)-3,4-dihydroxytetrahydrothiophen-2-yl)-9H-purine-6-ylamino)methyl)benzoic acid,
   (2R,3R,4S)-2-(2-chloro-6-methylamino-purin-9-yl)tetrahydrothiophen-3,4-diol,
   (2R,3R,4S)-2-(6-(3-fluorobenzylamino)-9H-purin-9-yl)tetrahydrothiophen-3,4-diol,
   (2R,3R,4S)-2-(6-(3-chlorobenzylamino)-9H-purin-9-yl)tetrahydrothiophen-3,4-diol,
   (2R,3R,4S)-2-(6-(3-bromobenzylamino)-9H-purin-9-yl)tetrahydrothiophen-3,4-diol,
   and
   (2R,3R,4S)-2-(6-(3-iodobenzylamino)-9H-purin-9-yl)tetrahydrothiophen-3,4-diol

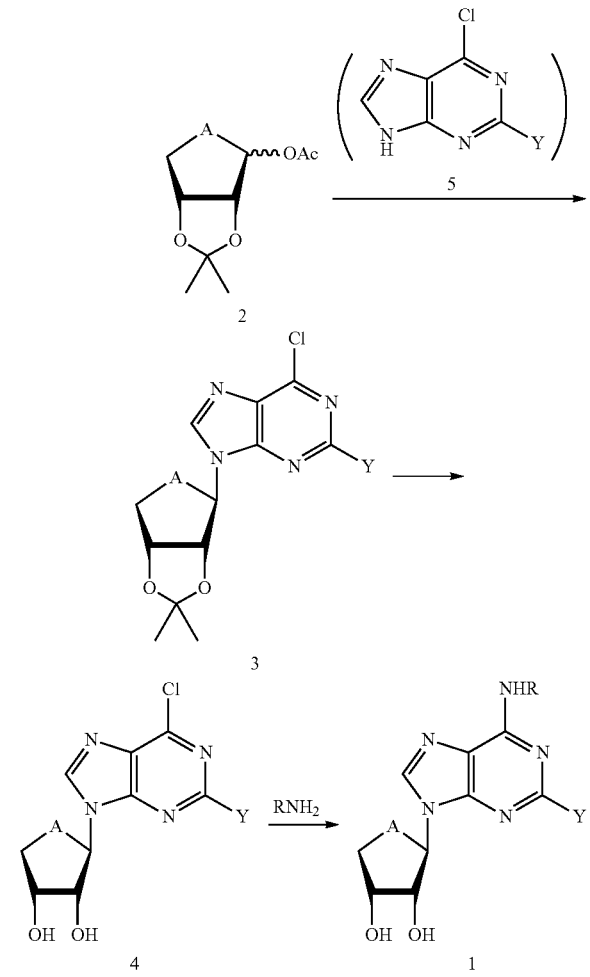

[Scheme 1]

wherein A is S, Y is Cl or H, R is methyl, 1-naphthylmethyl, 2-chlorobenzyl, 3-fluorobenzyl, 3-chlorobenzyl, 3-bromobenzyl, 3-iodobenzyl, 5-chloro-2-methoxybenzyl, 2-methoxybenzyl, or 3-toluic acid.

2. The method according to claim 1, wherein (1) is conducted in a solvent selected from the group consisting of dichloroethane, chloroform, acetonitrile and dichloromethane.

3. The method according to claim 1, wherein the Lewis acid of (1) is trimethylsilyl trifluoromethanesulfonate.

4. The method according to claim 1, wherein the silylated purine compound of (1) is prepared by reacting a purine compound of Chemical formula 5 with hexamethylsilazane in the presence of ammonium sulfate as a catalyst.

5. The method according to claim 1, wherein the catalyst of (3) is selected from the group consisting of triethylamine, pyridine, N,N-dimethylaminopyridine and 1,4-dioxane.

6. The method according to claim 1, wherein the starting material of Chemical formula 2 is prepared, as represented by the following Scheme 2, by:
(a₁) reacting D-mannose of Chemical formula 6 with 2,2-dimethoxypropane in the presence of an acid as catalyst to give a diacetonide compound of Chemical formula 7;
(a₂) subjecting the compound of Chemical formula 7 obtained in (a₁) to ring opening in the presence of a reducing agent to give a diol compound of Chemical formula 8;
(a₃) mesylating the compound of Chemical formula 8 obtained in (a₂) into a dimesyl compound of Chemical formula 9;
(a₄) cyclizing the compound of Chemical formula 9 obtained in (a₃) into a thiosugar compound of Chemical formula 10;
(a₅) selectively hydrolyzing the compound of Chemical formula 10 obtained in (a₄) into a diol compound of Chemical formula 11; and
(a₆) converting the compound of Chemical formula 11 obtained in (a₅) in the presence of a catalyst into an acetate compound of Chemical formula 2a

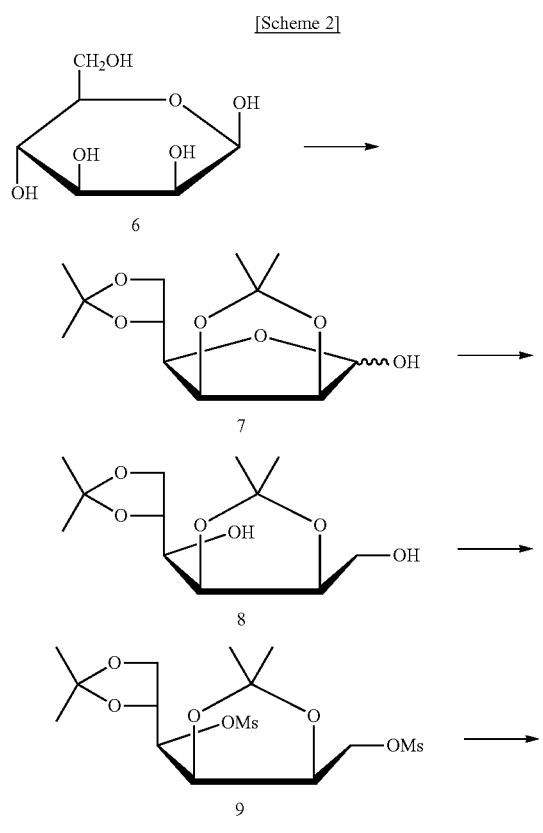

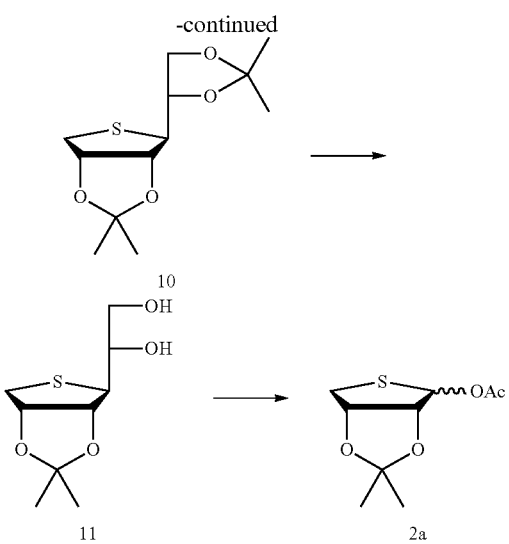

wherein compound 2a is identical to the compound of Chemical formula 2.

7. The method according to claim 6, wherein the catalyst of (a₁) is selected from the group consisting of concentrated sulfuric acid, hydrogen chloride, and p-toluene sulfonic acid.

8. The method according to claim 6, wherein the reducing agent of (a₂) is selected from the group consisting of sodium borohydride, lithium aluminum hydride and sodium sulfite.

9. The method according to claim 6, wherein the (a₃) is conducted in the presence of methanesulfonyl chloride as a mesylating agent.

10. The method according to claim 6, wherein the (a₄) is conducted in a solvent selected from the group consisting of ethyl ether, petroleum ether, dichloromethane, tetrahydrofuran and N,N-dimethylformamide.

11. The method according to claim 6, wherein the (a₅) is conducted in the presence of an acid selected from the group consisting of acetic acid, sulfuric acid, hydrochloric acid, and p-toluene sulfonic acid.

12. An A₃ adenosine receptor antagonist, comprising a (2R,3R, 4S) tetrahydrothiophen based adenosine derivative or a pharmaceutically acceptable salt thereof, wherein the (2R,3R,4S) tetrahydrothiophen based adenosine derivative is selected from the group consisting of:
(2R,3R,4S)-2-(2-chloro-6-(3-fluorobenzylamino)-9H-purin-9-yl)tetrahydrothiophen-3,4-diol,
(2R,3R,4S)-2-(2-chloro-6-(3-chlorobenzylamino)-9H-purin-9-yl)tetrahydrothiophen-3,4-diol,
(2R,3R,4S)-2-(6-(3-bromobenzylamino)-2-chloro-9H-purin-9-yl)tetrahydrothiophen-3,4-diol,
(2R,3R,4S)-2-(2-chloro-6-(3-iodobenzylamino)-9H-purin-9-yl)tetrahydrothiophen-3,4-diol,
(2R,3R,4S)-2-(2-chloro-6-(2-chlorobenzylamino)-9H-purin-9-yl)tetrahydrothiophen-3,4-diol,
(2R,3R,4S)-2-(2-chloro-6-(5-chloro-2-methoxybenzylamino)-9H-purin-9-yl)tetrahydrothiophen-3,4-diol,
(2R,3R,4S)-2-(2-chloro-6-(2-methoxybenzylamino)-9H-purin-9-yl)tetrahydrothiophen-3,4-diol,
(2R,3R,4S)-2-(2-chloro-6-(naphthalen-1-ylmethylamino)-9H-purin-9-yl)tetrahydrothiophen-3,4-diol,
3-((2-chloro-9-((2R,3R,4S)-3,4-dihydroxytetrahydrothiophen-2-yl)-9H-purine-6-ylamino)methyl)benzoic acid,
(2R,3R,4S)-2-(2-chloro-6-methylamino-purin-9-yl)tetrahydrothiophen-3,4-diol, (2R,3R,4S)-2-(6-(3-fluorobenzylamino)-9H-purin-9-yl)tetrahydrothiophen-3,4-diol, (2R,3R,4S)-2-(6-(3-chlorobenzylamino)-9H-purin-9-yl)tetrahydrothiophen-3,4-diol, (2R,3R,4S)-2-(6(3-bromobenzylamino)-9H-purin-9-yl)tetrahydrothiophen-3,4-diol, and (2R,3R,4S)-2-(6-(3-Iodobenzylamino)-9H-purin-9-yl)tetrahydrothiophen-3,4-diol.

13. A pharmaceutical composition for treatment of an inflammatory disease, comprising an (2R,3R,4S) tetrahydrothiophen based adenosine derivative or a pharmaceutically acceptable salt thereof, wherein the (2R,3R,4S) tetrahydrothiophen based adenosine derivative is selected from the group consisting of:

(2R,3R,4S)-2-(2-chloro-6-(3-fluorobenzylamino)-9H-purin-9-yl)tetrahydrothiophen-3,4-diol, (2R,3R,4S)-2-(2-chloro-6-(3-chlorobenzylamino)-9H-purin-9-yl)tetrahydrothiophen-3,4-diol, (2R,3R,4S)-2-(6-(3-bromobenzylamino)-2-chloro-9H-purin-9-yl)tetrahydrothiophen-3,4-diol, (2R,3R,4S)-2-(2-chloro-6-(3-iodobenzylamino)-9H-purin-9-yl)-3,4-diol;

(2R,3R,4S)-2-(2-chloro-6-(2-chlorobenzylamino)-9H-purin-9-yl)tetrahydrothiophen-3,4-diol, (2R,3R,4S)-2-(2-chloro-6-(5-chloro-2-methoxybenzylamino)-9H-purin-9-yl)tetrahydrothiophen-3,4-diol, (2R,3R,4S)-2-(2-chloro-6-(2-methoxybenzylamino)-9H-purin-9-yl)tetrahydrothiophen-3,4-diol, (2R,3R,4S)-2-(2-chloro-6-(naphthalen-1-ylmethylamino)-9H-purin-9-yl)tetrahydrothiophen-3,4-diol, 3-((2-chloro-9-((2R,3R,4S)-3,4-dihydroxytetrahydrothiophen-2-yl)-9H-purine-6-ylamino)methyl)benzoic acid, (2R,3R,4S)-2-(2-chloro-6-methylamino-purin-9-yl)tetrahydrothiophen-3,4-diol;

(2R,3R,4S)-2-(6-(3-fluorobenzylamino)-9H-purin-9-yl)tetrahydrothiophen-3,4-diol, (2R,3R,4S)-2-(6-(3-chlorobenzylamino)-9H-purin-9-yl)tetrahydrothiophen-3,4-diol, (2R,3R,4S)-2-(6-(3-bromobenzylamino)-9H-purin-9-yl)tetrahydrothiophen-3,4-diol, and (2R,3R,4S)-2-(6-(3-iodobenzylamino)-9H-purin-9-yl)tetrahydrothiophen-3,4-diol.

14. The pharmaceutical composition according to claim 13, wherein the inflammatory disease is selected from the group consisting of exudative inflammation, purulent inflammation, hemorrhagic inflammation, hyperplastic inflammation, and combinations thereof.

\* \* \* \* \*